United States Patent
MacDonald et al.

(10) Patent No.: US 10,525,283 B2
(45) Date of Patent: Jan. 7, 2020

(54) SYSTEMS AND METHODS FOR PLANNING AND CONTROLLING THE ROTATION OF A MULTILEAF COLLIMATOR FOR ARC THERAPY

(71) Applicant: DALHOUSIE UNIVERSITY, Halifax (CA)

(72) Inventors: Robert Lee MacDonald, Antigonish (CA); Alasdair Syme, Halifax (CA); Christopher G. Thomas, Halifax (CA)

(73) Assignee: Dalhousie University, Halifax (CA)

( * ) Notice: Subject to any disclaimer, the term of this patent is extended or adjusted under 35 U.S.C. 154(b) by 0 days.

(21) Appl. No.: 16/083,454

(22) PCT Filed: Mar. 9, 2017

(86) PCT No.: PCT/CA2017/050315
§ 371 (c)(1),
(2) Date: Sep. 7, 2018

(87) PCT Pub. No.: WO2017/152286
PCT Pub. Date: Sep. 14, 2017

(65) Prior Publication Data
US 2019/0030372 A1 Jan. 31, 2019

Related U.S. Application Data

(60) Provisional application No. 62/305,943, filed on Mar. 9, 2016.

(51) Int. Cl.
*A61N 5/10* (2006.01)

(52) U.S. Cl.
CPC ........... *A61N 5/1047* (2013.01); *A61N 5/103* (2013.01); *A61N 5/1049* (2013.01)

(58) Field of Classification Search
CPC .............................. A61N 5/1047; A61N 5/103
See application file for complete search history.

(56) References Cited

U.S. PATENT DOCUMENTS

| 5,651,044 A | 7/1997 | Klotz, Jr. et al. |
| 5,818,902 A | 10/1998 | Yu |
| (Continued) | | |

FOREIGN PATENT DOCUMENTS

| DE | 4324374 A1 | 12/1993 |
| EP | 2266664 A1 | 12/2010 |
| (Continued) | | |

OTHER PUBLICATIONS

Zhang, P. et al., "Optimization of collimator trajectory in volumetric modulated arc therapy: development and evaluation for paraspinal sbrt", International Journal of Radiation Oncology Biology Physics, vol. 77, No. 2 (2010): 591-599.

(Continued)

*Primary Examiner* — Kiho Kim
(74) *Attorney, Agent, or Firm* — Oyen Wiggs Green & Mutala LLP

(57) ABSTRACT

Systems and methods are provided for determining an angular trajectory for dynamically rotating a multileaf collimator during arc therapy. According to various embodiments, a suitable collimator trajectory may be determined based on the reduction or minimization of a residual unblocked area residing between a planning target volume and leaves of the multileaf collimator in the beam's eye view over the set of control points corresponding to an arc therapy plan. Various example methods are provided for determining collimator trajectories based on whitespace reduction, and for providing quantitative measures of whitespace optimization associated with a given trajectory. In some embodiments, the whitespace may be calculated using terms that (Continued)

account for the overlap of a planning target volume with an organ at risk of exposure.

39 Claims, 24 Drawing Sheets

(56) References Cited

U.S. PATENT DOCUMENTS

| | | | |
|---|---|---|---|
| 6,314,159 B1 | 11/2001 | Siochi | |
| 6,330,300 B1 | 12/2001 | Siochi | |
| 6,577,707 B2 | 6/2003 | Siochi | |
| 6,757,355 B1 | 6/2004 | Siochi | |
| 6,907,105 B2 | 6/2005 | Otto | |
| 6,999,556 B2 | 2/2006 | Nakano | |
| 7,496,173 B2 | 2/2009 | Goldman et al. | |
| 7,570,064 B2 | 8/2009 | Roziere | |
| 7,734,010 B2 | 6/2010 | Otto et al. | |
| 7,835,494 B2 | 11/2010 | Nord et al. | |
| 7,906,770 B2 | 3/2011 | Otto | |
| 8,416,917 B2 | 4/2013 | Maltz et al. | |
| 9,050,459 B2 | 6/2015 | Otto | |
| 9,283,405 B2 | 3/2016 | Wong | |
| 9,468,776 B2* | 10/2016 | Fredriksson | A61N 5/1031 |
| 9,861,834 B2* | 1/2018 | Xing | A61N 5/1031 |
| RE46,953 E * | 7/2018 | Yu | A61N 5/103 |
| 10,293,179 B2* | 5/2019 | Carpenter | A61N 5/103 |
| 10,315,045 B2* | 6/2019 | Peltola | A61N 5/1031 |
| 10,398,912 B2* | 9/2019 | Nord | A61N 5/1045 |
| 2003/0138078 A1 | 7/2003 | Eberhard et al. | |
| 2010/0260319 A1 | 10/2010 | Ein-Gal | |
| 2011/0091014 A1 | 4/2011 | Siljamaki et al. | |
| 2013/0142310 A1* | 6/2013 | Fahimian | A61N 5/103 378/65 |
| 2015/0231413 A1* | 8/2015 | Grady | A61N 5/1047 378/4 |
| 2018/0280725 A1* | 10/2018 | Sheng | A61N 5/1047 |
| 2019/0247676 A1* | 8/2019 | Peltola | A61N 5/103 |

FOREIGN PATENT DOCUMENTS

| | | |
|---|---|---|
| WO | 2007012185 A1 | 2/2007 |
| WO | 2016008052 A1 | 1/2016 |
| WO | 2016140955 A1 | 9/2016 |

OTHER PUBLICATIONS

Otto, K., "Volumetric Modulated Arc Therapy: IMRT in a Single Gantry Arc", Medical Physics vol. 35, No. 1, Jan. 1, 2008: 310-317, Abstract.

Blin, G. et al., "Towards unlocking the full potential of Multileaf Collimators", 40th International Conference on Current Trends in Theory and Practice of Computer Science (SOFSEM), Jan. 2014, High Tatras, Slovakia. 8327, pp. 138-149, 2013, Lecture Notes in Computer Science. <hal-00859708>.

Blin, G. et al., "Towards unlocking the full potential of Multileaf Collimators", Jan. 27, 2014, PowerPoint.

Jeraj, M. et al., "Multileaf collimator in radiotherapy", Radiol Oncol 2004, 38(3): 235-40.

Kim, Y.H. et al., "Effect of the Collimator Angle on Dosimetric Verification of the Volumetric Modulated Arc Therapy", Mar. 12, 2015.

Milette, M.-P., "Direct Optimization of 3D Dose Distributions Using Collimator Rotation", Thesis, The University of British Columbia, Jan. 2008.

Milette, M.-P. et al., "Maximizing the potential of direct aperture optimization through collimator rotation", Med Phys. Apr. 2007, 34(4):1431-8, Abstract.

Wu, Q. et al., "Optimization of Treatment Geometry to Reduce Normal Brain Dose in Radiosurgery of Multiple Brain Metastases with Single-Isocenter Volumetric Modulated Arc Therapy", Scientific Reports, Sep. 2016.

Webb, S., "Does the option to rotate the Elekta Beam Modulator MLC during VMAT IMRT delivery confer advantage?—a study of 'parked gaps'", Phys. Med. Biol. 55 (2010) N303-N319.

Yang, Y. et al., "Choreographicing Couch and Collimator in Volumetric Modulated Arc Therapy", Int. J. Radiation oncology Biol. Phys., vol. 80, No. 4, pp. 1238-1247, 2011.

* cited by examiner

Area 1 = 10 cm²
Area 2 = 10 cm²
Overlap = 2 cm²
$A_{PTV}$ = 18 cm²

FIG. 2L                    FIG. 2M

SYSTEMS AND METHODS FOR PLANNING AND CONTROLLING THE ROTATION OF A MULTILEAF COLLIMATOR FOR ARC THERAPY

CROSS REFERENCE TO RELATED APPLICATION

This application claims priority from U.S. application No. 62/305,943 filed 9 Mar. 2016. For purposes of the United States, this application claims the benefit under 35 U.S.C. § 119 of U.S. application No. 62/305,943 filed 9 Mar. 2016 and entitled SYSTEMS AND METHODS FOR PLANNING AND CONTROLLING THE ROTATION OF A MULTILEAF COLLIMATOR DURING VOLUMETRIC MODULATED ARC THERAPY which is hereby incorporated herein by reference for all purposes.

FIELD

The present disclosure relates to radiotherapy systems. More particularly, the present disclosure relates to the use of multileaf collimators in radiotherapy systems.

BACKGROUND

Linear accelerators used for radiotherapy delivery are equipped with a collimation system that is designed to block selected portions of the radiation beam. FIG. 1 shows an example collimator system 10 having two sets of orthogonally positioned jaws 110 and 115 positioned to limit the radiation beam aperture into a rectangular shape and a multileaf collimator (MLC) 100 having two banks of collimator leaves 120 and 125 which approach independently from the x-directions (in some collimator systems, the lower (x) jaws are replaced by the MLC). The controllable placement of each of the collimator leaves allows for more precise collimation with arbitrary shapes.

SUMMARY

Systems and methods are provided for determining an angular trajectory for dynamically rotating a multileaf collimator during arc therapy. Arc therapies include but are not limited to dynamic conformal arcs and volumetric modulated arc therapy. The approaches described herein are applicable to all types of arc therapy.

According to various embodiments, a suitable collimator trajectory may be determined based on the reduction or minimization of an objective function. The objective function may comprise or consist of a spatial measure corresponding to a residual unblocked area residing between a planning target volume and leaves of the multileaf collimator in the beam's eye view over a set of control points corresponding to an arc therapy plan. Various example methods are provided for determining collimator trajectories based on reduction or minimization of the spatial measure, and for providing quantitative measures of optimization associated with a given trajectory. In some embodiments, the spatial measure is calculated using terms that account for the overlap of a planning target volume with an organ at risk of exposure.

One aspect provides a radiation system comprising: a radiation source; a gantry, wherein said gantry is rotatable for varying a beam angle, relative to a subject, of a radiation beam produced by said radiation source; a multileaf collimator supported by said gantry, said multileaf collimator comprising a plurality of movable leaves for selectively altering a spatial profile of the radiation beam, wherein said multileaf collimator is rotatable relative to a beam axis of the radiation beam; a planning subsystem comprising computer hardware configured to: calculate, for each control point of a set of control points to be employed for generating an arc therapy plan, a plurality of spatial measures corresponding to a set of different collimator angles, wherein each spatial measure is based, at least in part, on a determination of a residual unblocked area residing between a planning target volume and leaves of said multileaf collimator, thereby generating two-dimensional spatial map data characterizing a dependence of the spatial measures on control point and collimator angle; process the spatial map data to determine a selected collimator trajectory that reduces or minimizes a sum of spatial measures accumulated over the set of control points, the selected collimator trajectory associating a single collimator angle with each control point; and generate, based on the selected collimator trajectory and the set of control points, the arc therapy plan; and a controller operably connected to said gantry, said multileaf collimator, and said planning subsystem. The controller is configured to: control said gantry such that said gantry is rotated according to the arc therapy plan; and control said multileaf collimator such that said multileaf collimator is rotated and positioned according to the arc therapy plan. In some embodiments the arc therapy plan is a volumetric modulated arc therapy plan.

Another aspect provides a computer-implemented method for determining a collimator trajectory for controlling a multileaf collimator of a radiotherapy device during arc therapy. The method comprises: calculating, for each control point of a set of control points to be employed for generating an arc therapy plan, a plurality of spatial measures corresponding to a set of different collimator angles of the multileaf collimator, wherein each spatial measure is based, at least in part, on a determination of a residual unblocked area residing between a planning target volume and leaves of the multileaf collimator, thereby generating two-dimensional spatial map data characterizing a dependence of spatial measures on control point and collimator angle; and processing the spatial map data to determine a selected collimator trajectory that reduces or minimizes a sum of spatial measures accumulated over the set of control points, the selected collimator trajectory associating a single collimator angle with each control point. In some embodiments the arc therapy plan is a volumetric modulated arc therapy plan.

Another aspect provides a method for controlling a radiotherapy device, the radiotherapy device comprising a radiation source, a rotatable gantry, and a multileaf collimator supported by the rotatable gantry, wherein the multileaf collimator is rotatable relative to a beam axis of a radiation beam produced by the radiation source. The method comprises: calculating, for each control point of a set of control points to be employed for generating an arc therapy plan, a plurality of spatial measures corresponding to a set of different collimator angles of the multileaf collimator, wherein each spatial measure is based, at least in part, on a determination of a residual unblocked area residing between a planning target volume and leaves of the multileaf collimator, thereby generating two-dimensional spatial map data characterizing a dependence of spatial measures on control point and collimator angle; processing the spatial map data to determine a selected collimator trajectory that reduces or minimizes a sum of spatial measures accumulated over the set of control points, the selected collimator trajectory associating a single collimator angle with each control point;

generating, based on the selected collimator trajectory and the set of control points, the arc therapy plan; controlling the gantry such that the gantry is rotated according to the arc therapy plan; and controlling the multileaf collimator such that said multileaf collimator is rotated and positioned according to the arc therapy plan.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the accompanying drawings.

FIG. 2A also shows a minimum bounding box fitted to the PTV. This example is for a single collimator angle and a particular embodiment in which the overlapping regions of OAR and PTV are factored into an algorithm used to determine the optimal collimator angle.

FIGS. 2L-2M illustrate the selection of collimator angle to reduce the contribution of interleaf leakage to whitespace.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The present disclosure provides systems and methods for the determination of a set of collimator angles for dynamically controlling the rotation of a multileaf collimator (MLC) during arc therapy. According to various example embodiments described herein, a set of collimator angles (hereafter referred to as a collimator trajectory), with each collimator angle corresponding to a different control point to be employed during arc therapy is determined based on the reduction, minimization, or optimization of an objective function.

Figure 1:
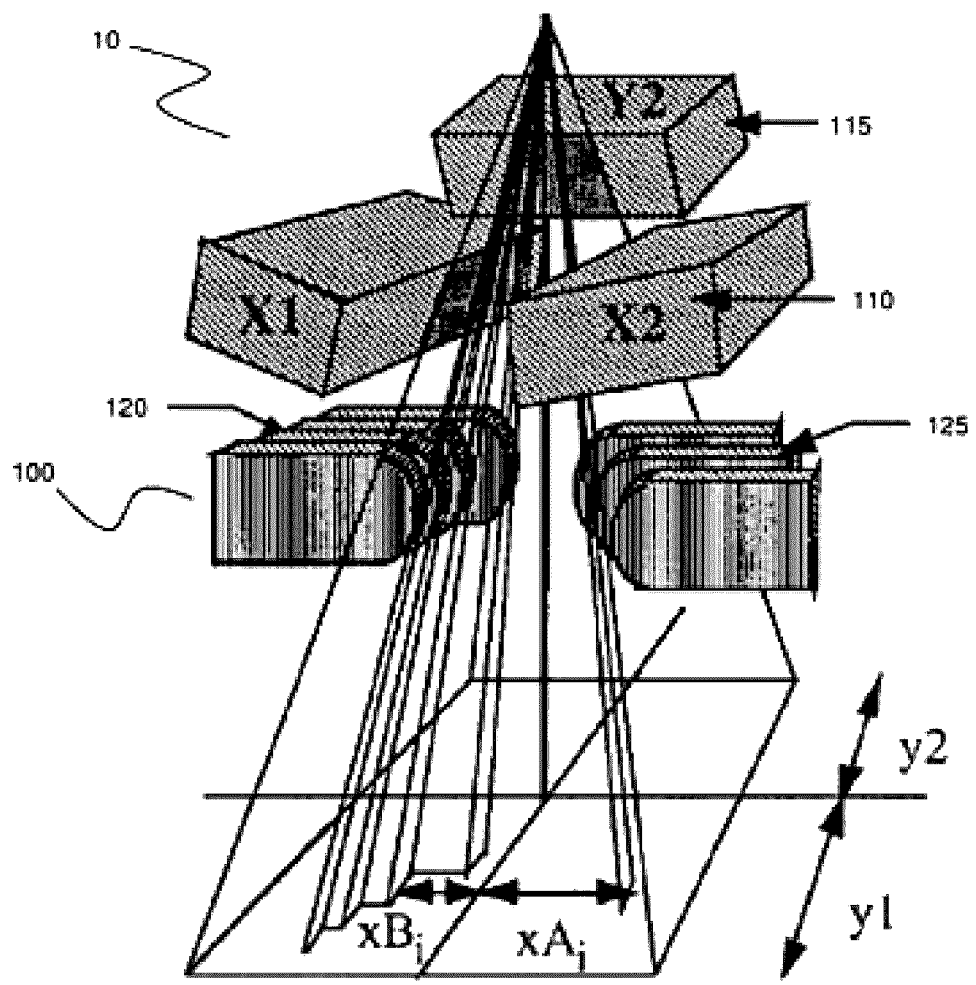
FIG. 1 is a schematic illustration showing the positions and orientations of the X and Y jaws and the multileaf collimator in an example radiation treatment system.

FIG. 1 is a schematic illustration showing the positions and orientations of the X and Y jaws and the multileaf collimator in an example radiation treatment system. The arrangement in FIG. 1 is typical of radiation treatment systems from Varian Medical Systems Inc. The methodology described herein is applicable to other MLC/jaw configurations.

In some embodiments the objective function comprises a spatial measure relating to unblocked radiation that is not directed at the planning treatment volume. Such a spatial measure may be called a "whitespace measure".

Another type of objective function measures a degree to which a direction of collimator leaf travel is orthogonal to a longest axis of the target volume (as determined by a technique such as principal component analysis). For example, Zhang, P et al. "Optimization of collimator trajectory in volumetric modulated arc therapy: development and evaluation for paraspinal sbrt." International Journal of radiation oncology biology physics. 77, no. s (2010): 591-599 doi:10.1118/1.2818738.doi:10.1016/j.ijrobp.2009.08.056 describes the use of principle components analysis to identify the orientation of a patient's spine. These or similar techniques may be used to identify the orientation of a longest axis of a PTV for a control point. An objective function may be built that assesses how closely the collimator leaves are to being perpendicular to this axis (or equivalently a degree to which the angle of the collimator leaves deviates from being perpendicular to the longest axis of the PTV).

New objective functions may be created by combining other objective functions (e.g. in a weighted sum). For example, an objective function may comprise a combination of a whitespace measure and a measure of alignment of collimator leaves perpendicular to the long axis of a PTV.

A "whitespace measure" may be understood as follows. In any radiation beam aperture, any point can be identified as belonging to one of the following regions: (i) the area collimated by the collimation system (which includes both jaws and MLC leaves), (ii) the area within the planning target volume (PTV), or (iii) the residual area, which is defined herein as "whitespace". Points within a beam aperture may be discretized into pixels with a finite resolution.

Accordingly, the phrases "whitespace" or "whitespace measure" may, in one example embodiment, refer to the area present in the beam's-eye-view (BEV) which is not blocked by a component of the collimation system, and is not within the target volume. Eqn. 1 is an example whitespace measure:

$$M_{WS}(\theta) = A_{Jaw,\theta} - A_{PTV} - A_{MLC,\theta} \quad (1)$$

Where $M_{WS}(\theta)$ is the value of whitespace at collimator angle $\theta$, $A_{Jaw,\theta}$ is the rectangular area defined by the minimum bounding box of the projected view of the planning target volume in the beam's eye view (BEV) at the defined collimator angle $\theta$, $A_{PTV}$ is the area of the PTV present in the current BEV, and $A_{MLC,\theta}$ is the total area within $A_{Jaw,\theta}$ blocked by the collimator leaves with the collimator leaves set to shape the radiation beam to fit the boundary of the PTV. It is presumed that the collimation system is configured to shape the radiation beam to fit the PTV (or PTVs) as closely as the design of the collimator system permits without occluding any part of the PTV. As such, with a few limiting exceptions (discussed in greater detail below), a suitable collimator angle may be determined by the reduction or minimization of whitespace. For example, a collimator angle corresponding to a minimized whitespace results in the collimation system being capable of fitting the radiation beam as tightly as possible to the PTV.

It is often the case that the planning target volume spatially overlaps with one or more organs when projected along the BEV at a given beam angle. In such cases, it can be a clinical priority to minimize dose to such an organ at risk (OAR) within the BEV, in order to prevent healthy critical structures from being collaterally harmed during the course of treatment. It can therefore be advantageous to explicitly consider areas of overlap between an OAR and the PTV in the definition of whitespace for a particular BEV. When whitespace is defined in this manner and collimator angle selection is based on minimization of whitespace, then pixels in these overlapping areas will make an explicit contribution to the optimization process.

Figure 2A:
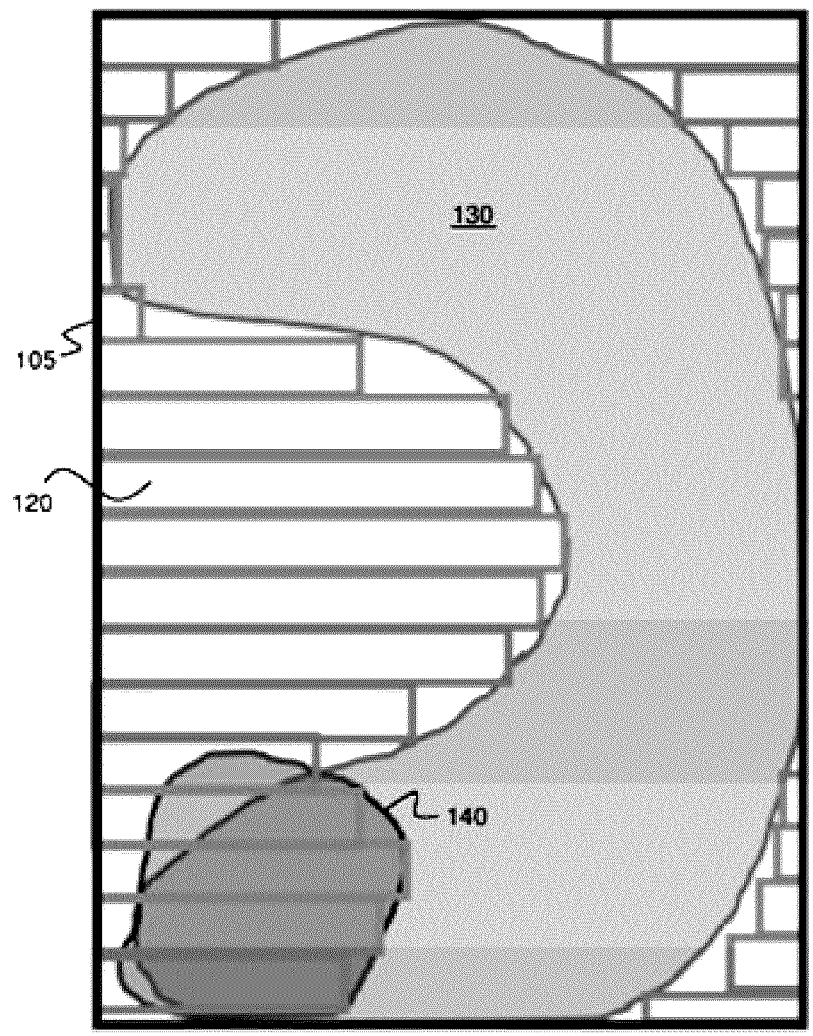
FIG. 2A shows an example of an aperture assessed for collimation, showing the relative areas in a beam's eye view occupied by a planning target volume (PTV), an organ at risk (OAR), and the aligned collimator leaves collimating the defined PTV.

For example, FIG. 2A shows a BEV perspective of a spatial region that is addressable by the multileaf collimator. The angle of the multileaf collimator may be defined based on rotation of the multileaf collimator around a central axis of the radiation field (the beam axis). The ability of the multileaf collimator 100 to block radiation dosage to organs-at-risk of exposure (OARs) while treating the planning target volume (PTV) is dependent on this angle. FIG. 2A shows the relative areas occupied by an example planning target volume (PTV) 130, an organ at risk of exposure (OAR) 140, and the area of the aligned collimator leaves 120 collimating the defined PTV. Box 105 indicates the minimum bounding box fitted to the PTV. This example shows a configuration for a single collimator angle, at a single beam angle of the gantry.

Figure 2B:
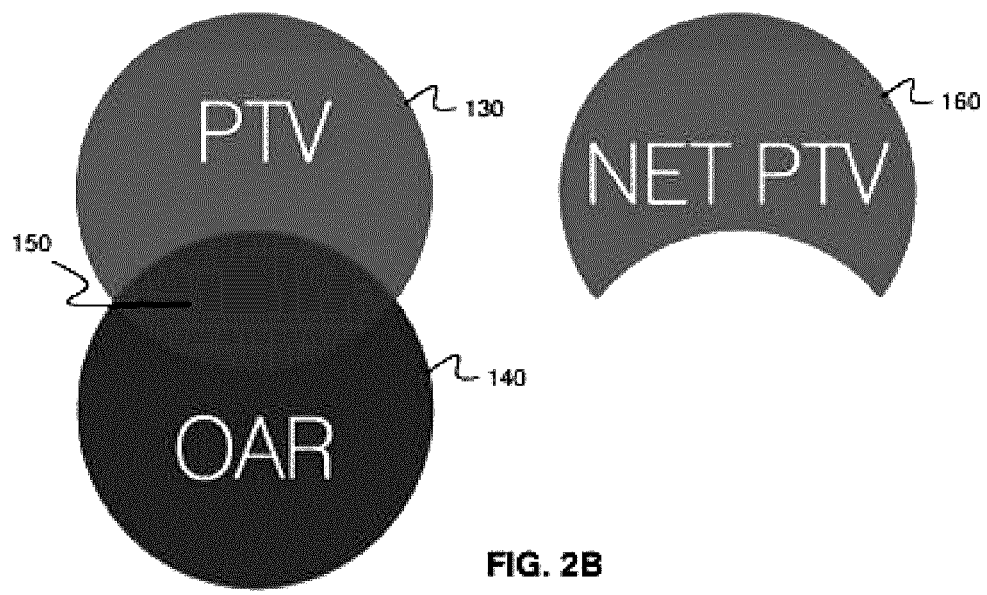
FIG. 2B illustrates the subtraction, from the PTV, of the spatial region over which the PTV overlaps with the OAR.

FIG. 2B shows schematically the area of PTV 130, the OAR 140, a region 150 of overlap between PTV 130 and the OAR 150, and an area 160 which is the PTV with overlap region 150 subtracted. Area 160 may be called a "NetPTV".

In cases in which an OAR is overlapping with the PTV, a suitable whitespace measure may be defined as follows, where the area of the PTV that is included in the calculation is the NetPTV. This creates the following example alternative definition for the spatial measure referred to herein as the whitespace measure:

$$M_{WS}(\theta) = A_{Jaw,\theta} - A_{NetPTV} - A_{MLC,\theta} \quad (2)$$

where $M_{WS}(\theta)$ is the value of whitespace at collimator angle $\theta$, $A_{Jaw\theta}$ is the rectangular area defined by the minimum bounding box of the projected view of the planning target volume in the beam's eye view at the defined collimator angle $\theta$, $A_{NetPTV}$ is the area of the NetPTV, and $A_{MLC\theta}$ is the total area within $A_{Jaw,\theta}$ blocked by the collimator leaves with the collimator leaves set to shape the radiation beam to fit the boundary of the PTV (except when the PTV boundary is involved in an overlap with an OAR, in which case the collimator leaves are set to shape the radiation beam to fit the boundary of the NetPTV).

Figure 2C:
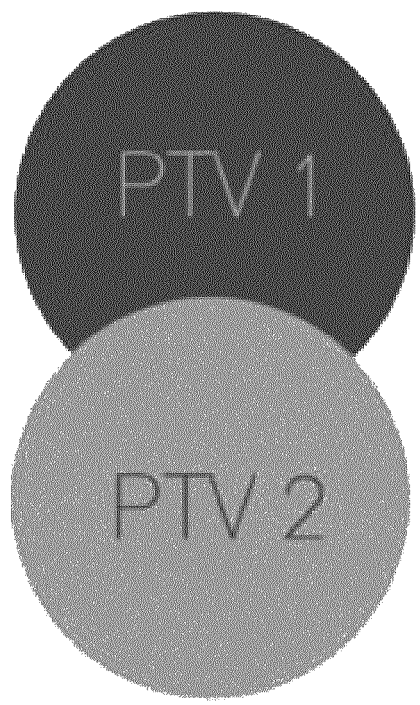
FIG. 2C shows an example with multiple PTVs that spatially overlap.

In some cases, multiple PTVs or different parts of a single PTV may themselves overlap within the BEV (see, for example, FIG. 2C). In such cases, the PTV area $A_{PTV}$ in equations (1) and (2) may be made equal to the summed area of targets or regions, with the area of any overlap of the targets or regions subtracted. Alternatively, all projected PTVs may be combined and represented as one structure for the whitespace calculations.

In another example embodiment, one or more weighting factors or functions may be included in equation (2). For example, the following equation may be employed for the determination of whitespace:

$$M_{WS}(\theta) = w_1 A_{Jaw\theta} - (w_2 A_{PTV} - w_3 A_{PTV \cap OAR}) - w_4 A_{MLC\theta} \quad (3)$$

In Eqn. (3), the quantity $A_{NetPTV}$ has been expressed as the difference between $A_{PTV}$ and $A_{PTV \cap OAR}$ to allow greater flexibility in providing weighting factors or functions ($w_2$ and $w_3$ respectively) to the constituent parts of $A_{NetPTV}$. In equation (3) one or more of the weighting terms may be unity.

The weighting terms in equation (3) may optionally be selected so proximal overlapping pixels are masked out, but distal overlapping pixels are left in.

Where there are two or more OARs some of the OARs may be more important to spare from radiation than others. In some embodiments, weighting factor $w_3$ is a function which selectively includes only more important OARs. For example, some of the OARs may have a parameter value of 0 and $w_3$ may exclude contributions to the overlap for such OARs. This may be useful when there are many OARs that overlap, and only the contribution of some of the OARs is to be considered. A user may selectively assign parameter values to the OARs by way of a suitable user interface.

Figure 2D:
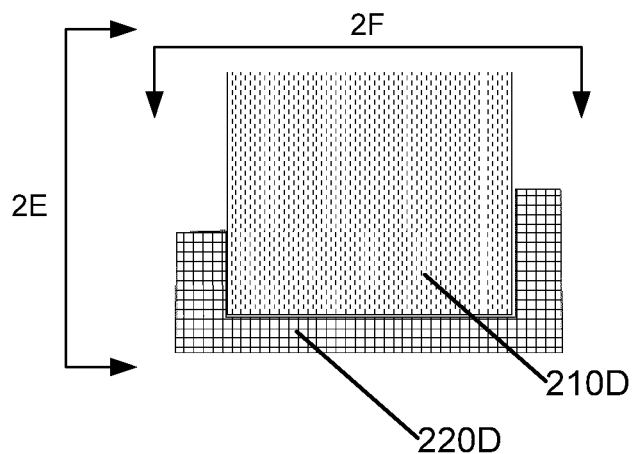
FIGS. 2D-2H illustrate the effect of the relative location of the OAR on the configuration of the collimator. These figures illustrate different ways in which an algorithm could determine the shape to which the MLC leaves should conform and identifies areas that will contribute to white space when they are not covered by the MLC.
Figures 2E, 2F:
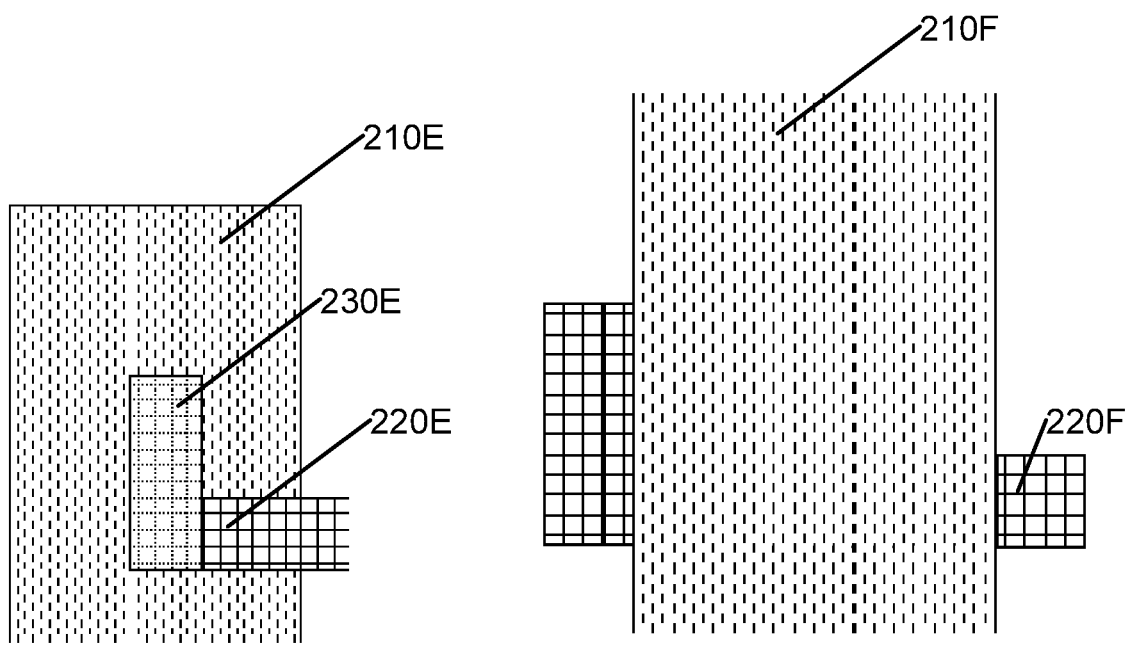
Figure 2G:
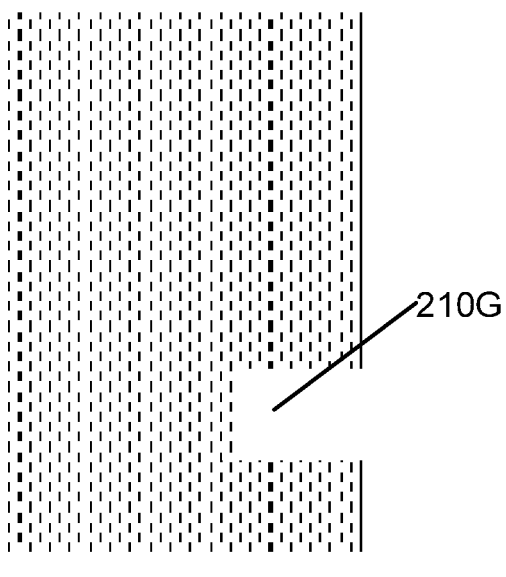
Figure 2H:
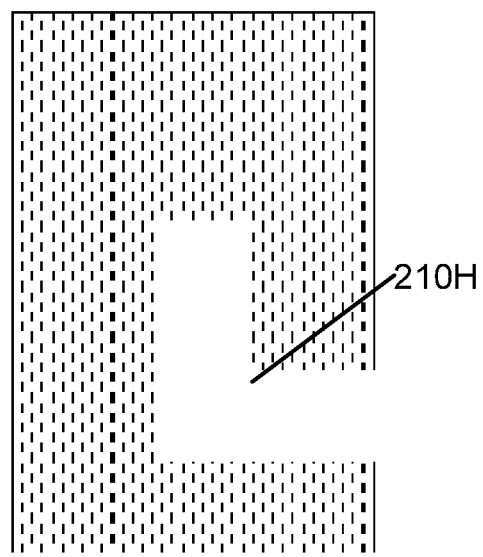

In some embodiments, a consideration of the spatial orientation of the OARs relative to the PTV may provide a means of weighting the importance of optimal collimator angle for OAR shielding purposes relative to optimal collimator angle for PTV conformality. FIGS. 2D-2F illustrate the effect of the relative location of the OAR in the configuration of the collimator. FIGS. 2D-2F show three views of a tumor/OAR combination, in which a PTV (target volume—210D, 210E and 210F) is partially surrounded by an OAR (220D, 220E and 220F). FIG. 2D shows a first top view, and FIG. 2E shows a first side view along line 2E shown in FIG. 2D. FIG. 2F shows a second side view along line 2F shown in FIG. 2D.

For the beam angle corresponding to FIG. 2E, the OAR lies both in front of the PTV and behind it. Region 230E indicates distal pixels that are purely behind (i.e. distal to) the target volume, whereas the region 220E indicates regions in which there are OAR pixels that are either exclusively proximal to the PTV or both proximal AND distal to the PTV. In this case, it may be desirable to be able to conform the MLCs to the shape 210E defined by the PTV minus the proximal OAR region 220E. This may be the case for several reasons, but one dosimetric reason is that the area of the OAR that is on the proximal side of the PTV to the radiation source will be receiving a higher dose than the corresponding area of the PTV because of the way in which high energy photon beams deposit their energy. If a binary mask is applied to this beam's eye view in which all pixels are subtracted from the PTV in which there is proximal overlap with the OAR, the resultant shape would take the form shown in FIG. 2G. Conversely, if all pixels of the OAR had been masked, which is another option, the resultant shape would take the form shown in FIG. 2H. In FIGS. 2G and 2H, 210G and 210H indicate areas that will contribute to white space when they are not covered by the MLC.

Which of these options is chosen has implications for collimator angle optimization based on whitespace. If the distal voxels of the OAR are far enough from the PTV, exit dose may be a smaller concern than other factors in the planning process. By using the function $w_3$ to mask out only proximal overlapping voxels of the OAR from the PTV, the system may factor this consideration into its determination of minimal whitespace. The situation becomes much more complex in the planning of treatments for certain disease sites (for example, head and neck cancer) in which there are many OARs. In this case, it might become very important to limit the number of pixels that are masked out of the PTV. Consideration of spatial orientation of OARs versus PTV is a useful tool for accomplishing this. In some implementations a planning system is configured to allow the planner to identify those OARs considered sufficiently important for a particular patient's treatment plan and to include only those OARs for consideration in this masking process.

In some embodiments, the weighting parameter $w_4$ can serve to reduce the dose to the patient due to interleaf leakage, which can occur due to the shape of the collimator leaves. This radiation leakage effect is illustrated in FIGS. 2I-2K.

Figure 2I:
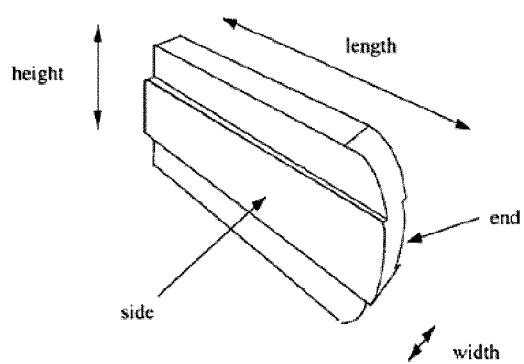
FIG. 2I shows the structure of a single collimator leaf.
Figure 2J:
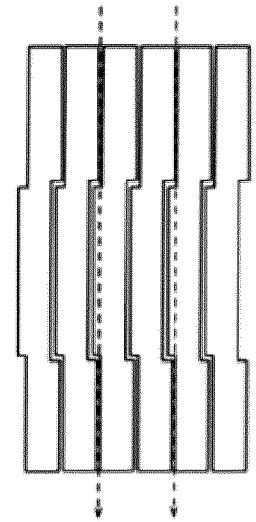
FIG. 2J shows a bank of collimator leaves from an end-on perspective.
Figure 2K:
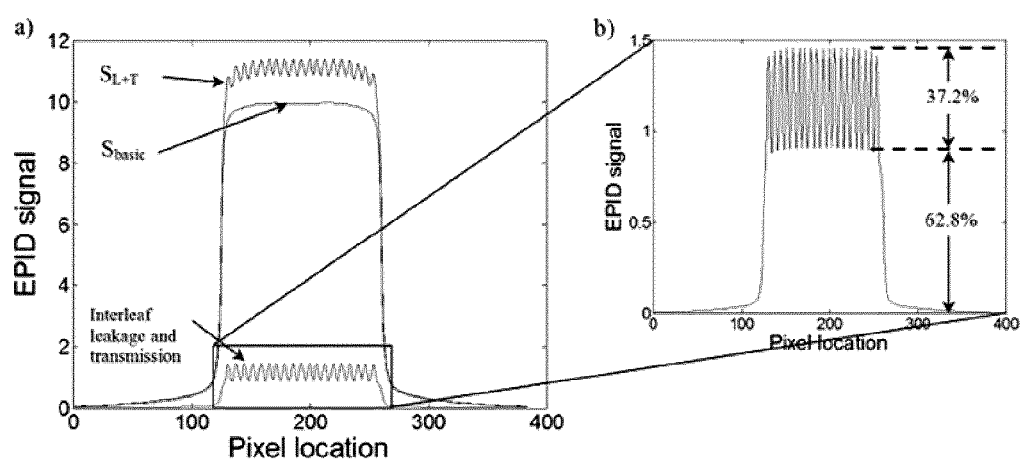
FIG. 2K shows the effect of interleaf leakage on the delivered dose profile.

FIG. 2I shows the structure of a single collimator leaf, and FIG. 2J shows a bank of collimator leaves, looking from an end-on perspective. As can be seen in FIG. 2J, the discretization of collimator leaves provides narrow paths for radiation through the multileaf collimator between neighbouring leaves in which the attenuation by the material of the leaves (typically tungsten) is reduced. The consequence is a dose profile in the direction perpendicular to leaf travel such as the dose profile shown in FIG. 2K. In FIG. 2K, periodic variations in dose are caused by interleaf leakage. These variations are undesirable. It may be desirable to reduce the magnitude of this effect by minimizing the area shielded by the MLC.

For example, $w_4$ may take the following form:

$$w_4 = (1 - \alpha) \quad (4)$$

where $\alpha$ is a parameter compensating for interleaf leakage. The first term inside the parentheses acts on $A_{MLC\theta}$ to reduce whitespace by the area shielded by the MLC at collimator angle $\theta$. The second term can then be used to penalize the whitespace calculation due to the inclusion of unnecessarily large areas of MLC shielding by effectively adding back a portion of the whitespace area.

Use of an additional term to account for interleaf leakage is illustrated in FIGS. 2L and 2M. In the absence of the a term in the function $w_4$, both of the apertures shown in FIGS. 2L and 2M would produce effectively the same whitespace value because every pixel inside the bounding box (i.e. the jaw-defined area of the radiation field) is either covered by collimator leaves or PTV (in other words, $A_{PTV} + A_{MLC\theta} = A_{Jaw\theta}$) (also there is no OAR in this example so the third term in the whitespace function of equation (3)

is zero). By adding the a term, the collimator angles that introduce excessive multileaf collimator leakage are penalized in an effort to reduce patient dose due to interleaf leakage.

Figure 2N:
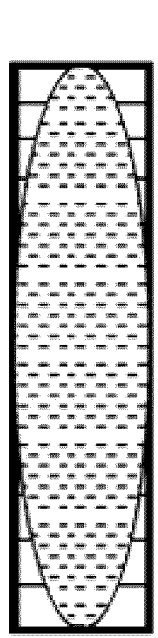
FIG. 2N shows example plots of part of the value of the term $w_4$.
Figure 2N:
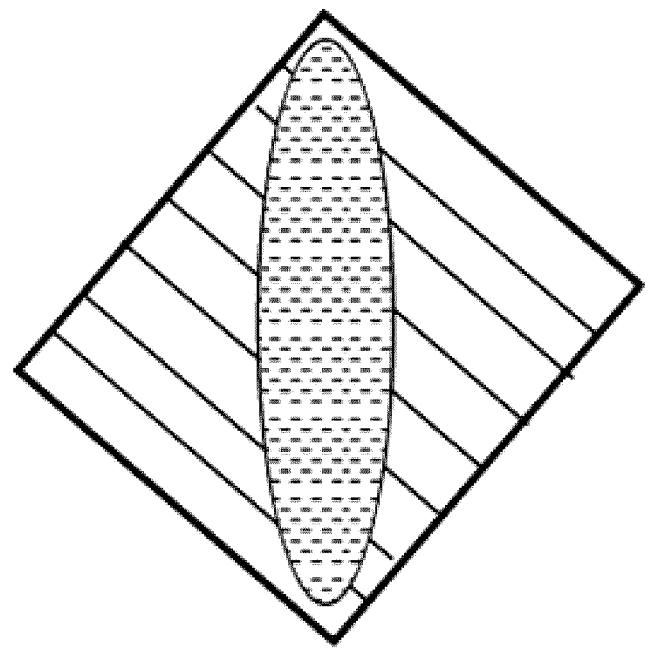
Figure 2N:
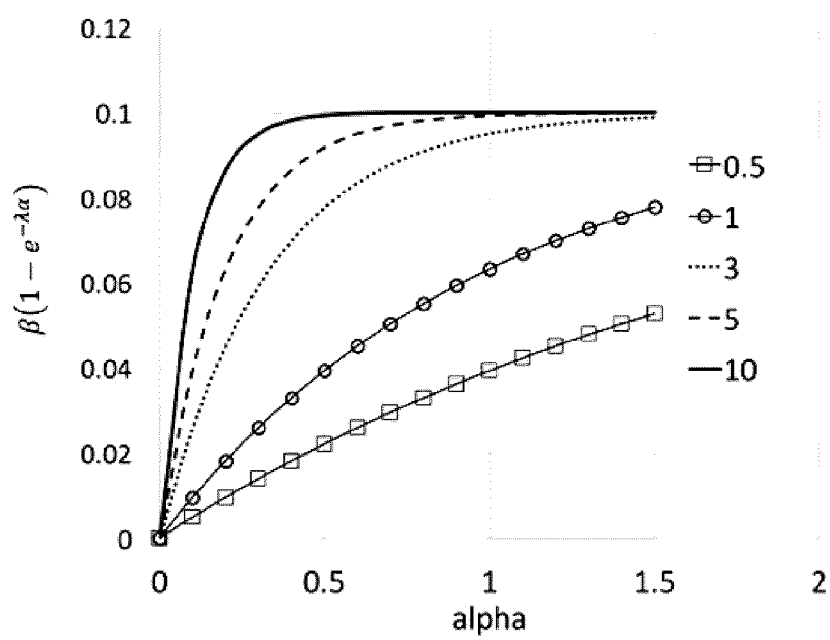

Another example functional form for the parameter $w_4$ is as follows:

$$w_4 = 1 - \beta(1 - e^{-\lambda\alpha}) \quad (5)$$

where:

$\beta$ is a term that limits the maximum impact of the excessive MLC shielding on the overall whitespace value; and $\lambda$ is a term that governs how quickly the function will reach the maximum value assigned by $\beta$;

$\alpha$ may, for example, be given by:

$$\alpha = \frac{\left(\frac{A_{jaw\theta}}{A_{PTV}}\right) - \left(\frac{A_{jaw\theta'}}{A_{PTV}}\right)}{\left(\frac{A_{jaw\theta'}}{A_{PTV}}\right)} \quad (6)$$

which simplifies to:

$$\alpha = \frac{A_{jaw\theta} - A_{jaw\theta'}}{A_{jaw\theta'}} = \frac{A_{jaw\theta}}{A_{jaw\theta'}} - 1 \quad (7)$$

where:

$A_{jaw\theta'}$ = The area of the minimum possible bounding box $A_{jaw\theta}$ = The area of the bounding box at the collimator angle $\theta$ The value of alpha would be 0 if the jaw size is the minimum possible bounding box. The term from w4 given by:

$$\beta(1 - e^{-\lambda\alpha}) \quad (8)$$

has the form shown in FIG. 2N when $\beta$ has a value of 0.1.

In this example, this function can then effectively penalize the component of the whitespace score derived from multileaf collimator shielding by a maximum of 10% for excessive shielding. The choice of 10% is in this case arbitrary and a clinically optimal value could be determined from clinical planning studies.

Other functional forms of $w_4$ are also possible that produce similar limiting behaviours. Another such form is:

$$w_4 = 1 - \beta\left(\frac{1}{1 + \frac{1}{\lambda\alpha}}\right) \quad (9)$$

During instances of successive control points in which there is a superposition of MLC interleaf leakage within a given plane of the patient's anatomy, collimator rotation can be perturbed from the optimized collimator angle in order to mitigate the superposition. Superposition of interleaf leakage can lead to "stripes" of excessive radiation dose being deposited in the patient, which in turn require the dose optimization algorithm to compensate, thereby potentially resulting in a sub-optimal treatment plan. Examples of causes of superposition are:

1. couch and collimator stationary, with collimator at 0 degrees, and gantry rotating about patient;
2. gantry stationary, couch and collimator are rotating at same rate and in respective directions that render the couch motionless in the frame of reference of the collimator (i.e. from the collimator's point of view, the couch does not appear to be moving).

There may be other instances in MLC superposition can occur, but those presented here are to serve only as potential examples.

Techniques for this perturbation include:

1. an offset from 0 degrees in the collimator angle during instances such as those described in 1 above;
2. an oscillatory, periodic motion of the collimator angle about the idealized trajectory over this region of control points. In instances described in 2 above, a constant offset of collimator angle would not eliminate superposition of interleaf leakage, it would simply alter the plane in which the leakage is superimposed.

In some situations, the efficiency of the treatment delivery may be improved by orienting the collimator such that the direction of travel of the MLC leaves is perpendicular to the longest axis of the PTV in a given BEV. Methods for determining the longest axis of the PTV may include, for example, principal component analysis (PCA). In embodiments described hereafter, it will be understood that PCA is an example and is not limiting or exclusionary of other methods. Eqn. (10) is an example of a more generalized expression for the objective function associated with collimator angle selection at a given control point:

$$OF = (w_{WS} * M_{WS}) + (w_{PCA} * M_{PCA}) + \ldots + (w_n * Mn) \quad (10)$$

Where: OF is the total objective function, $w_{ws}$ is the weighting factor for the whitespace metric, $M_{WS}$ is the whitespace metric (as defined for example in one of Eqn. (1) to Eqn. (3)), $w_{PCA}$ is the weighting factor for the metric derived from PCA, $M_{PCA}$ is an example of a collimator suitability metric derived from principal component analysis in which the collimator suitability is measured as the deviation of the collimator angle from that of the angle perpendicular to the longest axis measured from the BEV data for the target projection, and $w_n$ is the weighting factor for the $n^{th}$ metric, Mn. In these generalized terms, the objective function used to orient the collimation system is based on a combination (e.g. the weighted sum) of n metrics each with strengths in different clinical contexts.

Eqn (11) is one specific example of an objective function of the type provided by Eqn. (10):

$$OF = (w_{WS} * M_{WS}) + (w_{PCA} * M_{PCA}) \quad (11)$$

Where the terms are defined above. In this example, the objective function is the weighted sum of whitespace and a metric based on principal component analysis of the target projection. Each of these metrics carries differing importance in clinical contexts, and the weighting factors $w_{ws}$ and $w_{PCA}$ could be, in some embodiments, user-defined weighting values interpretable by planning experts to tailor the contribution of each metric in the overall cost equation. In some embodiments, these weighting values could serve to also normalize each of the metrics in order to define the total range of values found by each metric to a defined range (e.g. the range from 0 to 1).

The weighting factors in Eqns. (10) and (11) may be determined based on the type of arc therapy being planned in some embodiments. In clinical scenarios in which Eqn. (10) or (11) is implemented and the arc therapy technique selected is dynamic conformal, the whitespace metric would have importance as the leaves are fit to the boundary of the target for the duration of treatment. In such a scenario, $w_{ws}$ ought to be much larger than $w_{PCA}$. In clinical scenarios in which Eqn. (10) or (11) is implemented and the arc therapy technique selected is volumetric modulated arc therapy, the $w_{PCA}$ would have importance as the treatment should benefit from the collimator orientation being perpendicular to the longest axis of the target, as required leaf-travel during modulation would be minimized. In such a scenario, $w_{PCA}$ may be selected to have a value comparable to that of $w_{ws}$.

In systems according to some embodiments, values for weighting factors for different metrics or allowable ranges for such values may be set automatically based at least in part on a selection of a type of arc therapy being planned.

In various embodiments described below, using whitespace as a metric, at each control point (e.g. BEV) present in the treatment plan, the relative suitability of a collimator angle can be assessed, and a suitable collimator angle trajectory can be generated that provides a prescription of the dynamic rotation of a multileaf collimator during execution of an arc therapy plan. As noted above, a collimator trajectory is a set of collimator angles, where each collimator angle corresponds to a different control point of an arc therapy plan.

Non-limiting example methods for generating arc therapy plans include: 1) Otto, Karl. "Volumetric Modulated Arc Therapy: IMRT in a Single Gantry Arc." Medical Physics 35, no. 1 (Jan. 1, 2008): 310-17. doi:10.1118/1.2818738.): a first step in which the gantry trajectory will be specified for the treatment planning system (i.e. through what angular range it will travel). The gantry trajectory can be considered as a series of discrete, static fields, instead of a dynamic motion. Each one of these discrete fields is defined at a control point. A VMAT plan can also involve the specification of the couch angle at each one of those control points.

The systems and methods described herein enable the subsequent determination of a suitable or preferred collimator angle at each control point (i.e. each control point that was identified in the first step described above). According to several example embodiments, this collimator angle trajectory definition is a step that takes place after the couch/gantry trajectory has already been defined, but before the plan is generated through inverse optimization.

Once the gantry trajectory and collimator trajectory have been provided to the treatment planning system (e.g. a VMAT planning engine or module), an inverse optimization algorithm can be employed to identify the spatial configuration of the MLC aperture at each control point in order to achieve the pre-defined goals of the treatment plan. The aperture realized by the optimization algorithm will necessarily respect the constraints imposed by the control point-specific collimator angle that was pre-determined by an algorithm of the type described herein.

Unlike intensity modulated radiotherapy (IMRT), in which a set of one or more different collimator angles may be sequentially employed at a given beam angle in order to deliver a prescribed two-dimensional spatial fluence pattern at a given beam angle, the embodiments disclosed herein that pertain to arc therapy may involve the delivery of a single aperture for each beam angle (or couch angle/position), where the single aperture has a two-dimensional fluence pattern that is not modulated by MLC leaf motions.

Various example systems and methods of the present disclosure process a two-dimensional map of a metric (e.g. an objective function such as whitespace data) to select a suitable collimator trajectory that reduces or minimizes an objective function (e.g. accumulated whitespace or accumulated value of another objective function) over the trajectory. For example, two-dimensional whitespace map data may be generated by calculating, for each control point associated with a predetermined arc therapy plan, a plurality of whitespace measures corresponding to a set of different collimator angles.

Such a map may be represented as a 3-dimensional data structure in which points on a surface are defined by control point, collimator angle and the corresponding value of the objective function.

As noted above, each whitespace measure is based, at least in part, on a determination of a residual unblocked area residing between a planning target volume and leaves of the multileaf collimator. Accordingly, such two-dimensional whitespace map data characterizes a dependence of whitespace on control point and collimator angle. In cases in which the control points are directly mapped to gantry/beam angles, the two-dimensional whitespace map data characterizes a dependence of whitespace on gantry/beam angle and collimator angle.

For each allowable collimator angle at a defined control point, the positions of the MLC leaves may be calculated based on the location of intersection of an MLC leaf with the net PTV (for example, as shown in FIG. 2B). Since an MLC leaf could intersect the net PTV at multiple positions along its travel path, the selected position may be selected as that which corresponds to the smallest distance travelled by each leaf from its most retracted position. The contour of the net PTV in the beam's-eye-view is projected to the plane of the machine isocentre (which, for many common treatment machines is 100 cm) since MLC positions are specified in units of distance measured at isocentre. The contour of the PTV will have been previously specified, for example using software with tools specifically designed for that purpose (e.g. the contouring tools in the Eclipse™ treatment planning system from Varian Medical Systems). Most often, the contour of the PTV is specified by a qualified individual on a series of contiguous images from, for example a CT (computed tomography) data set. A rendering of the 3D volume is then used to visualize a 2D projection of the PTV in the beam's-eye-view.

The MLC positions at each collimator angle and each control point may optionally be stored such that they can be recalled in a rapid manner. However, once a whitespace value has been calculated for each combination of control point and collimator angle, the MLC leaf positions used in the calculation of whitespace values may no longer be required in the planning process. Actual leaf positions in a final arc treatment plan may be specified based on the results of an inverse optimization process. This process is initiated after the collimator trajectory has been specified according to the algorithms described herein.

Figure 3A:
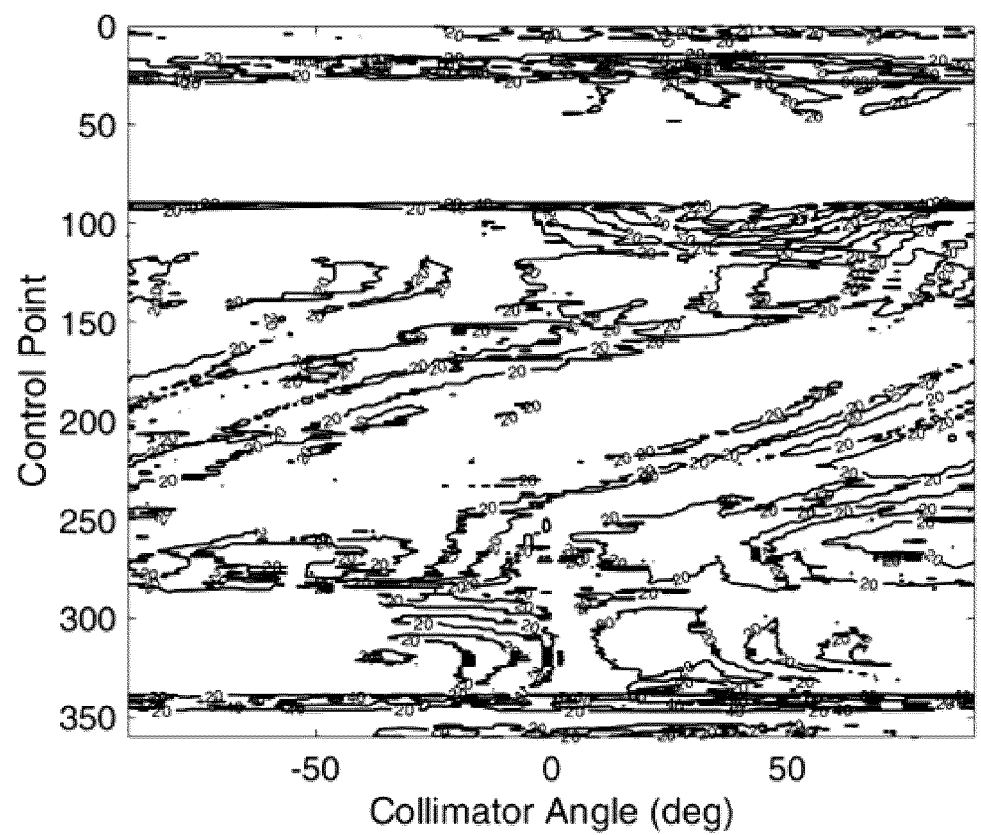
FIG. 3A is an example plot of a raw-value whitespace map for a patient with an acoustic neuroma.

FIG. 3A is a plot of example whitespace map data. The vertical axis shows control point (uniquely defined by gantry angle and couch rotation angle) and the horizontal axis shows collimator angle. The contour lines on the map provide a measure of whitespace, where high values correspond to angles which collimate poorly, leaving high amounts of whitespace, and low values are well-collimated angles. The whitespace map plotted in FIG. 3A is based on whitespace map data generated based on an acoustic neuroma treatment plan.

Figure 3B:
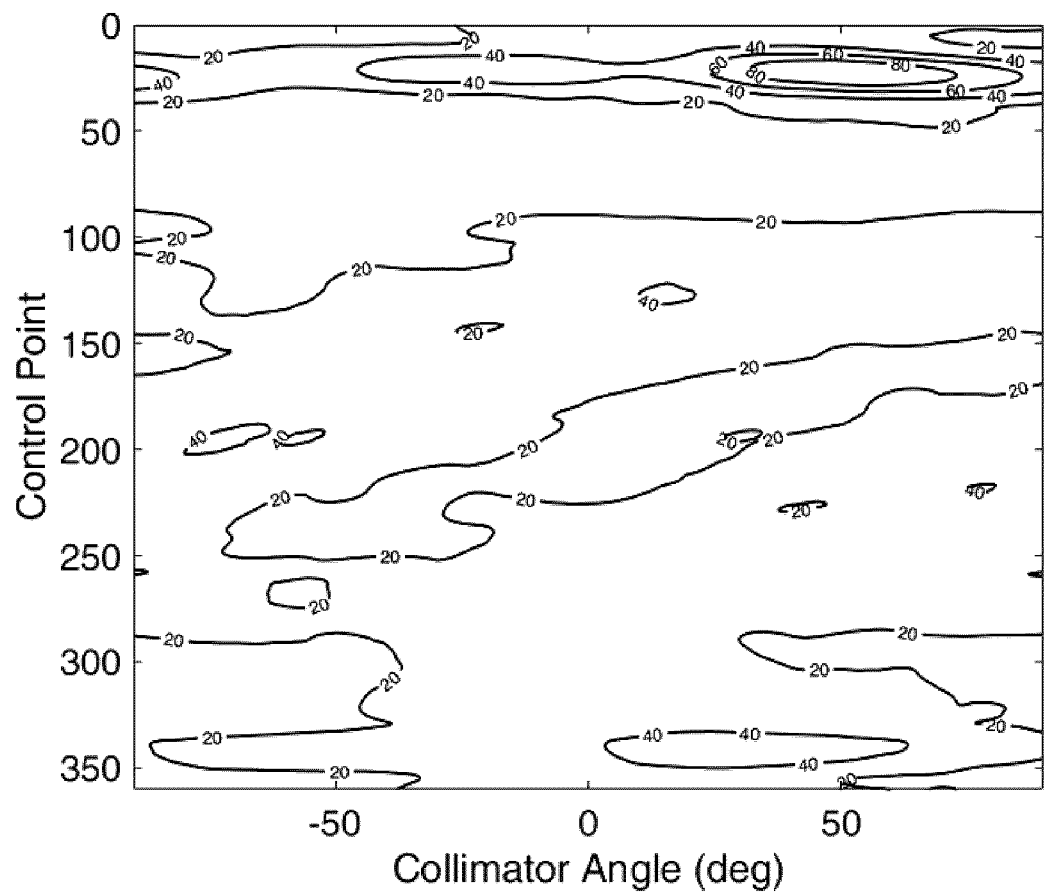
FIG. 3B plots the same whitespace map as shown in FIG. 3A, normalized to the highest value of whitespace, and low-pass filtered with a 10 pixel radius Gaussian filter.

It may be useful to contextualize the whitespace map data to differentiate sections where whitespace deviates very little with changing collimator angle from sections where collimator angle is highly consequential. This may be achieved, for example, by normalizing the whitespace map to the highest global whitespace value. Additionally, sharp discontinuities are typically present in a whitespace map due to the finite width of the collimator leaves. For example, as a collimator leaf is included or removed between collimator angles, the value of the whitespace measure decreases or increases, respectively, as discontinuity. The local changes in topography may confound the global changes in topography, and can be smoothed, for example, by the application of a low-pass filter to the map in order to generate smooth topography for navigation. FIG. 3B displays the same whitespace map as that shown in FIG. 3A, normalized and low-pass filtered with a Gaussian filter of radius equal to 10-pixels. While this example used a 10-pixel radius Gaussian filter, other filter functions may be used. For example, the radius and filter function of this filter can vary with the width required to filter sharp discontinuities in whitespace resulting from the discretized nature of the MLC leaves, while preserving major trends of the map.

As noted above, a two-dimensional map of whitespace data may be processed to select a suitable collimator trajectory that reduces or minimizes the accumulated whitespace over the trajectory. Such a collimator trajectory provides coordinates for the collimator angle rotation throughout treatment. It will be understood that there are a wide variety of methods of processing the two-dimensional whitespace map data in order to identify or select a suitable trajectory for reducing or minimizing whitespace. Various non-limiting examples of such methods are provided below.

According to various example embodiments, one or more collimator trajectories may be determined by constraining a change in collimator angle between two successive beam angles to be less than a maximum angular range. The maximum angular range may be selected to be less than an achievable angular range that is achievable based on the rotation speed of said multileaf collimator, such that collimator trajectory is determined based on dosimetric constraints, as opposed to mechanical constraints. For example, the maximum angular range may be selected to be two degrees, even though the collimator may be capable of undergoing a rotation greater than two degrees between successive control points.

The aforementioned method in which the maximum angular range is determined based on dosimetric considerations for arc therapy, such that the determination is independent of the maximum speed of rotation of the collimator, can be contrasted with methods in which a mechanical constraint is placed on allowable change in collimator angle based on elapsed time between control points and knowledge of the maximum velocity of the collimator. For example, in treatments with a large number of monitor units (e.g. high dose, single fraction stereotactic radiosurgery procedures for brain tumors), the gantry slows down and the elapsed time between control points can be sufficiently large that large angular displacements of the collimator may be permitted between control points. In contrast to such methods, the present example embodiment is based on restricting allowable collimator motions based on dosimetric considerations.

For example, the maximum angular range may be determined based on treatment planning calculation algorithms. Such algorithms (e.g. Progressive Resolution Optimization from Varian Medical Systems) restrict the amount of movement (of, for example the gantry, or in our case, the collimator) between control points because the dose calculation is based on the static beam aperture defined at the control point (i.e. there is no consideration of what happens dosimetrically between control points).

Figure 4A:
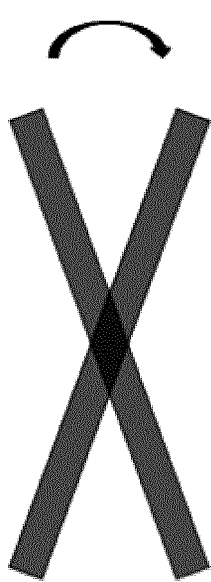
FIGS. 4A-4D illustrate the effect of the angular change in collimator angle (between control points) on the discrepancy between planned dose (FIGS. 4A, 4B) and delivered dose (FIGS. 4C, 4D) for two different collimator rotation ranges.
Figure 4B:

This can be understood with reference to FIGS. 4A-4D. In FIG. 4A, a sample collimator trajectory is presented for a thin rectangular beam. The collimator rotates through an angle of 40 degrees between the two control points (the use of a 40 degree rotation between control points is meant to illustrate the concept rather than an example of what might actually be planned). In FIG. 4B, the same rectangular beam rotates through an angle of 2 degrees between the two control points. FIGS. 4A and 4B represent the dose distribution that would be calculated by a treatment planning system, because the system would only consider the two discrete, static positions of the collimator.

Figure 4C:
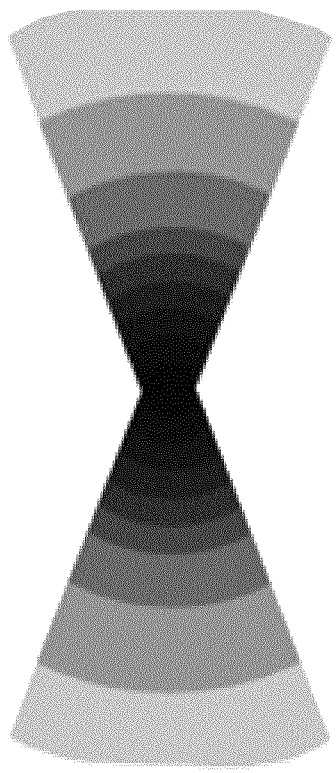
Figure 4D:

FIGS. 4C and 4D represent the dose distributions that would actually be delivered by the treatment machine for the trajectories shown in FIGS. 4A and 4B, respectively. In the present example, the radiation produced by the treatment machine is continuously emitted while the collimator is rotating. This will have the effect of blurring the dose distribution so that it extends from one defined aperture to the other. These figures clearly show that there is substantial similarity between FIGS. 4B and 4D and substantial discrepancy between FIGS. 4A and 4C. It can therefore be important to restrict collimator motions between control points based on dosimetric considerations rather than mechanical considerations.

In one example implementation, a "brute-force" approach may be employed to identify a suitable collimator trajectory. For example, using a randomly selected starting point on the whitespace map, a trajectory may be randomly designed such that collimator angle motion from one control point to the next does not differ by a maximum angular range (two degrees in the present example implementation), as described above. The randomly defined trajectory may then be assessed based on its total accumulated whitespace and total movement of the collimator throughout.

In an example prototype embodiment, this random generation of trajectory was permuted a number of different times (e.g. 10, 100, 1,000, and 10,000 times) and the best solution (with the minimum accumulated whitespace) was saved. This process was repeated 100 times for each permutation level, and the results of the calculation area plotted in FIG. 5 (see points marked "Random Anchor Point", which lie above the points marked "Best Anchor Point").

Figure 5:
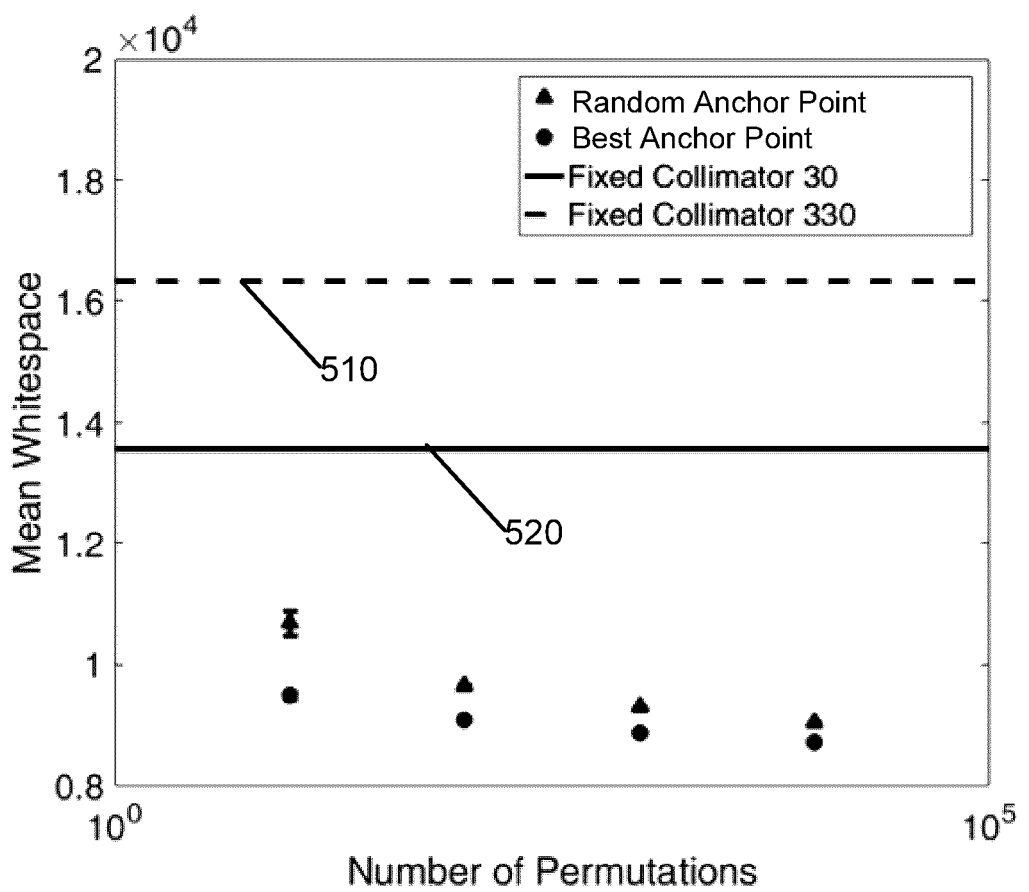
FIG. 5 plots results of 100 repetitions of a brute-force design approach with increasing permutations.

In FIG. 5, The upper points show the results from the entirely random trajectory selection method, and the lower points show the results from the random trajectory selection method with the constraint of passing through the highest ranking anchor point. Lines 510 and 520 indicate the accumulated white space in the conventional fixed collimator angles of 330° and 30°, respectively. The results for each permutation level were compared to the conventionally selected fixed collimator angles of 30 degrees and 330 degrees for accumulated whitespace, showing the degree to which random brute-force selection can improve this process.

In order to further improve the quality of the randomly selected trajectories, higher-quality starting points may be identified for generating the random trajectories. These strong candidate starting points are henceforth referred to as "anchor points". An anchor point, refers to the collimator angle that corresponds to the smallest whitespace value for a control point. In a hierarchical ranking of anchor points, the "Best anchor point" refers to the anchor point located at the control point containing the global maximum whitespace value in the whitespace map data. Subsequent anchor points in the hierarchy may be derived in a similar manner, but the search for subsequent global maximum whitespace values no longer includes those control points that have already been used to identify a previous anchor point. Anchor points can be introduced or removed in the design of the trajectory based on their ranking.

In one example implementation, the brute-force method described above may be adapted to force the starting point of the random trajectory to be the highest ranking anchor point. This causes the trajectory to pass through the anchor point of the highest quality, missing the global maximum on the map, with all other points in the trajectory being random, provided that they follow the previously defined rules for continuity. This alternative method was employed for the example shown in FIG. 5. The mean whitespace values for 100 repetitions of each permutation level are shown, with standard error used as uncertainty.

Figure 6:
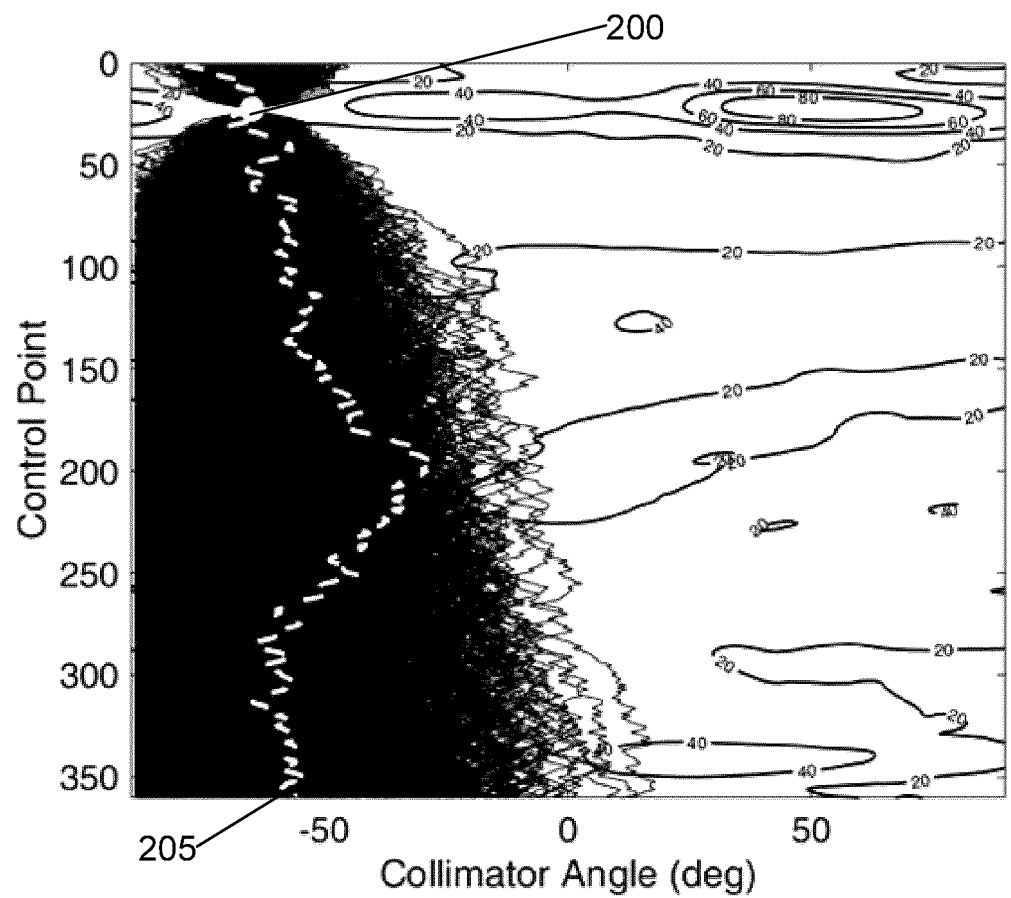
FIG. 6 plots an overlay of the anchor point brute-force approach.

FIG. 6 shows an overlay of all of the calculated random trajectories on the whitespace map, where all random trajectories pass through the anchor point 220. One thousand permutations are shown. The selected trajectory minimizing the accumulated whitespace is indicated by 205.

Figure 7:
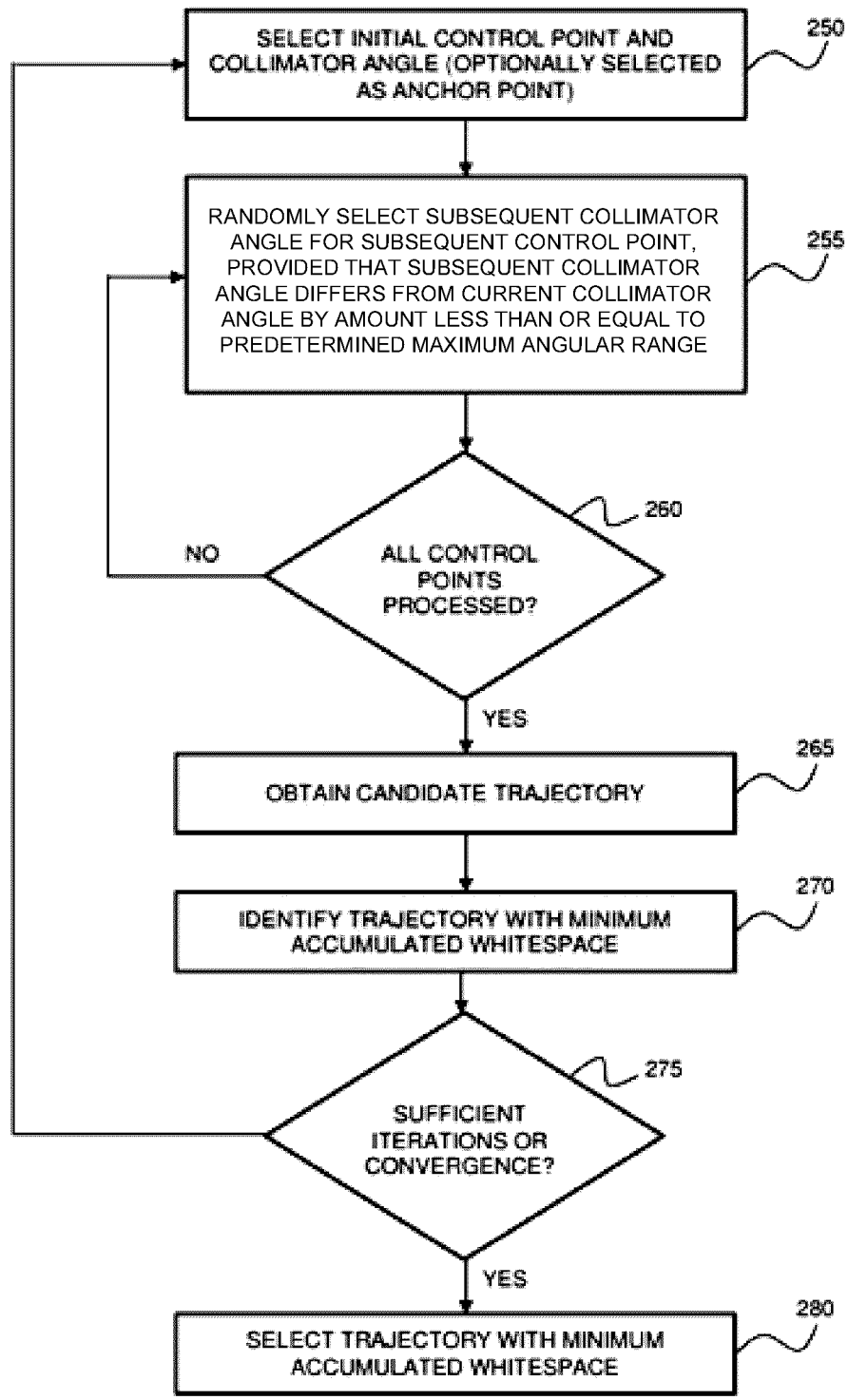
FIG. 7 is a flow chart illustrating an example method of generating a collimator trajectory based on a random trajectory generation.

FIG. 7 is a flow chart illustrating an example method of determining a suitable collimator trajectory by generating and assessing random trajectories. In step 250, an initial control point and collimator angle are selected. This control point and collimator angle may be an anchor point, as described above, or may be a randomly selected combination of control point and collimator angle.

In step 255, a subsequent collimator angle for an adjacent control point is randomly selected, provided that the collimator angle for the adjacent control point differs from the current collimator angle by an amount that is less than or equal to a predetermined maximum angular range. This process may then be repeated for all control points, as shown at step 260, in order to obtain a full candidate trajectory at step 265.

The process shown in steps 250-265 may then be repeated to generate a set of additional candidate trajectories, identifying, each time a new candidate trajectory is generated, the trajectory with the minimum accumulated whitespace, as shown at 270. This process may be repeated until a preselected criterion has been satisfied, such as a minimum number of iterations, or a suitable convergence in the minimum accumulated whitespace. Finally, as shown in step 280, the candidate trajectory with the lowest accumulated whitespace is selected as the collimator trajectory, as shown at step 280.

Figure 8:
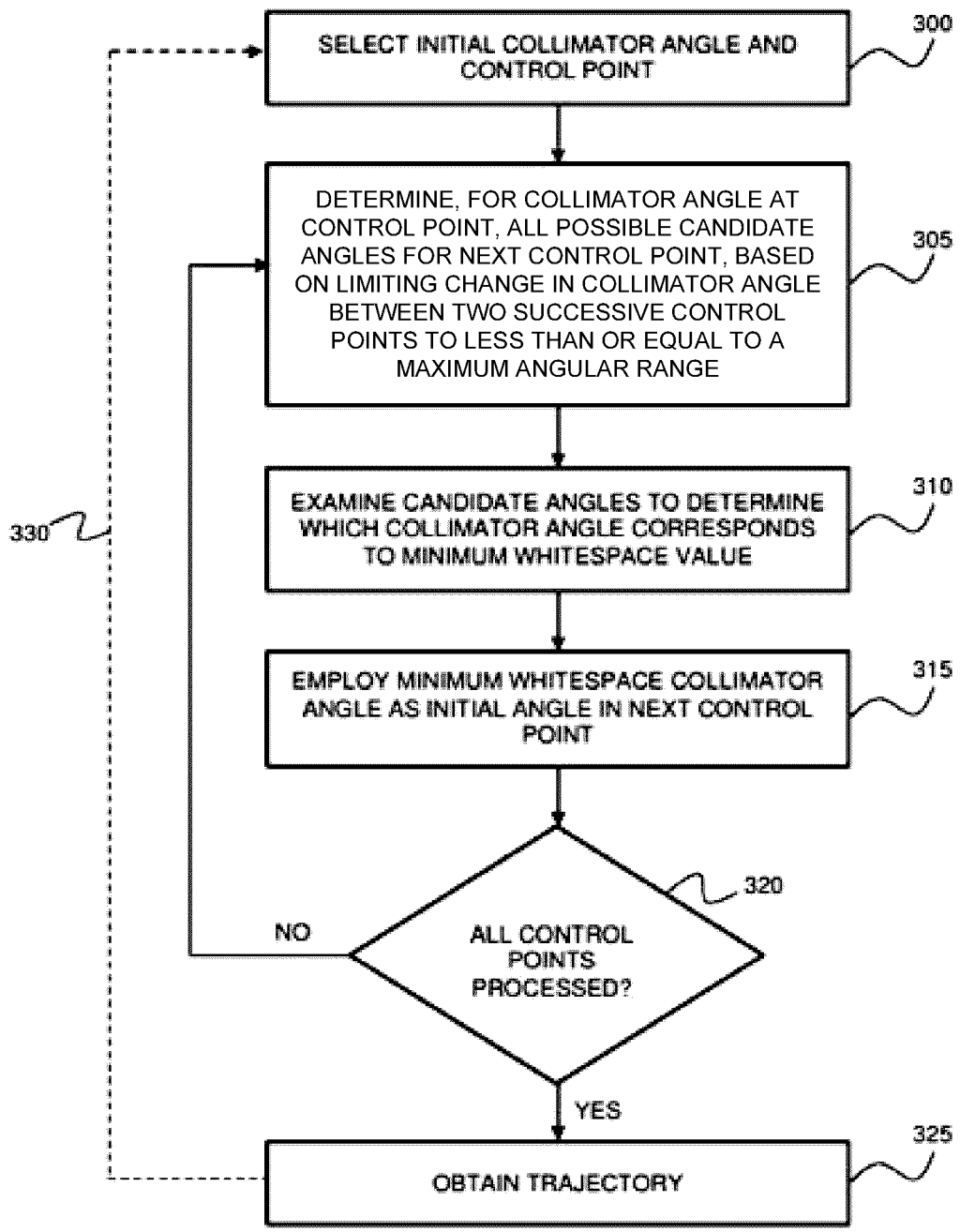
FIG. 8 is a flow chart illustrating an example method of generating a collimator trajectory based on a gradient calculation.

In an alternative example embodiment for selecting a suitable collimator trajectory, a gradient-based method is employed to progressively search for a trajectory of collimator angles that minimizes an objective function (e.g. accumulated whitespace or another objective function as described herein). Referring to the flow chart shown in FIG. 8, the method may be performed as follows. An initial pair of control point and collimator angle is selected in step 300. In step 305, all possible candidate angles for the next control point are determined, based on limiting the change in collimator angle between two successive control points to less than or equal to a maximum angular range (e.g. two degrees, as previously described). As shown at steps 310 and 315, the candidate angles may then be examined to determine which of the candidate collimator angles corresponds to the minimum whitespace value. This minimum whitespace angle may be selected as the collimator angle for the subsequent control point.

This process may then be repeated for all control points, as shown at step 320, in order to obtain a full trajectory at step 325. It is noted that in order to generate a full trajectory over all control points using this method, the initial control point should be the first (for a forward gradient calculation) or the last control point (for a reverse gradient calculation). Alternatively, an intermediate control point may be selected, with collimator angles for the forward set of control points being determined using a forward gradient method, and collimator angles for the preceding set of control points being generated using a reverse gradient method. The use of bi-directional gradients is described in further detail below.

Figure 9A:
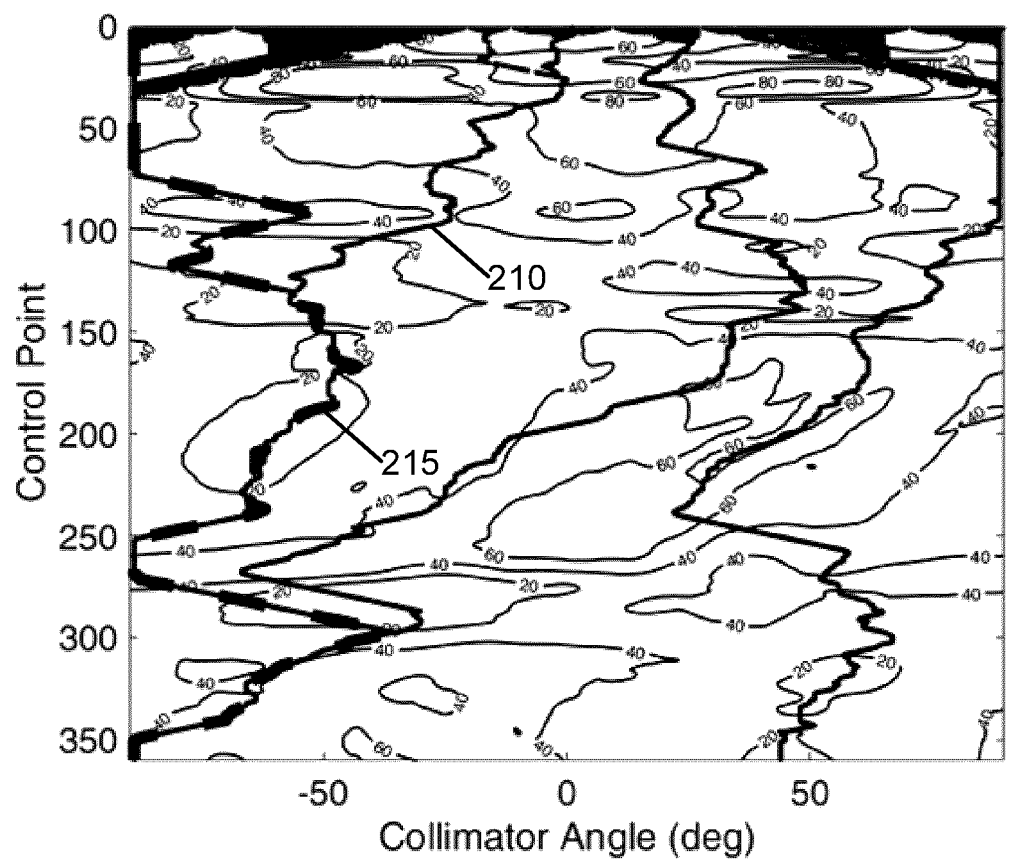
FIG. 9A plots the overlaid trajectories of all 180 possibilities of the minimum gradient search algorithm in an example implementation involving a collimator angular resolution of 1°.

As shown by the dashed line 330, this process may be repeated for multiple initial collimator angles, in order to obtain a set of trajectories. The trajectory with a minimized accumulated whitespace may be selected. This method effectively follows the path of least resistance throughout the trajectory for every possible starting angle. An example implementation of this method is shown in FIG. 9A, in which the trajectories identified by this gradient method are overlaid on a whitespace map. It can be seen that the trajectories generated for each initial collimator angle rapidly converge to several trajectories (e.g. 210 and 215).

When compared to the brute force approach, the anchor point-defined random selection permuted 100,000 times reached an accumulated whitespace score of 8617 (normalized units) with the sum of the absolute value of the gradient of the total collimator angle (used as the metric to define the continuity of the trajectory) of 301 degrees. This calculation took 253 seconds. The algorithmically defined gradient solution was found in 12 seconds, had a whitespace value of 8500, and a continuity metric value of 281 degrees. Using the gradient search defined algorithm exceeded the best comparable benchmark, as the solution was 3% better (i.e. smaller) in terms of whitespace, 95.3% faster, and 7% smoother in terms of total collimator motion.

It will be understood that the collimator trajectory selection methods described above are provided to illustrate example and non-limiting methods, and that other minimization or optimization methods may be employed in the alternative.

In order to further ensure that a given solution is finding the minimized portions of the whitespace map, the whitespace map data may be processed to identify angles for each control point (rows of the map) which have whitespace values that are less than a threshold. The threshold may be determined relative to a minimum whitespace value, for example, a threshold may be selected to be 20% higher than the local minimum. This calculation results in the identification of portions of the whitespace map data that are suitable for trajectory design, and may be more useful than merely presenting only the collimator angle corresponding to minimum whitespace value for each row, which can hide the extent to which a portion of the map has low whitespace value. The present example method identifies islands within the whitespace map of areas ideal for passage of collimator trajectories.

Figure 9B:
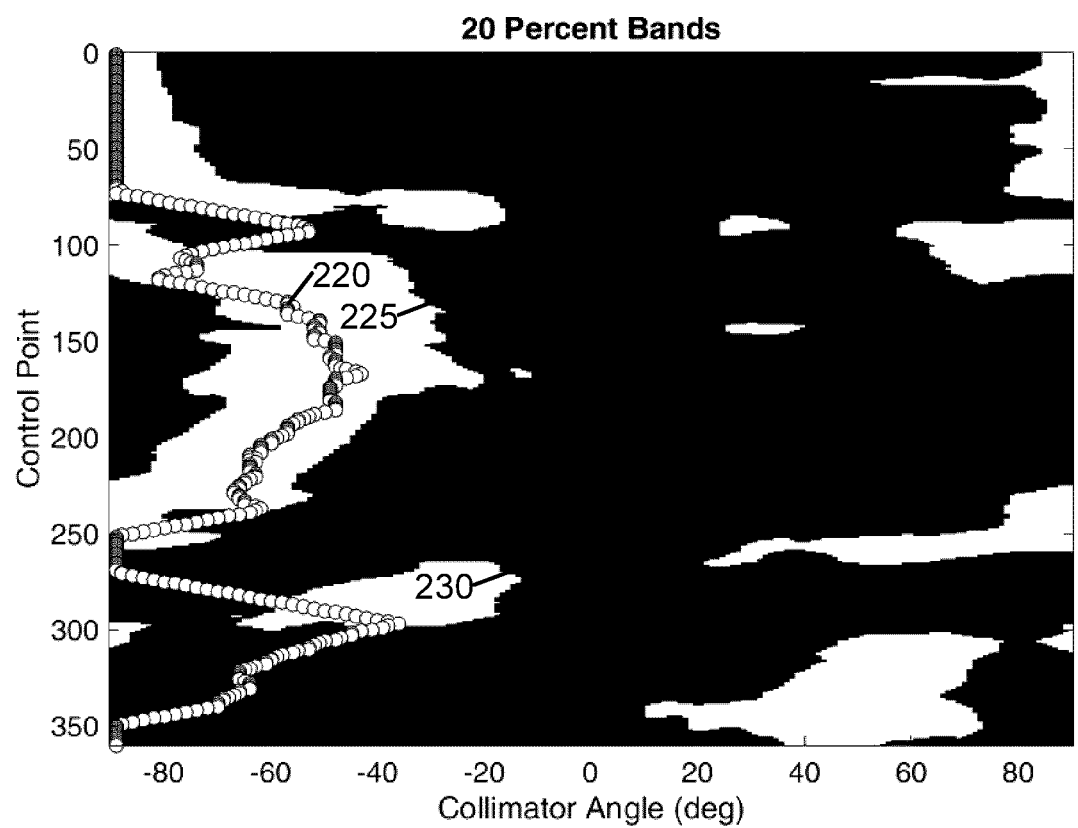
FIG. 9B plots an example of a whitespace map truncated to display the sections of the map which correspond to within 20% of the local minimum.

An example implementation of this method, using 20% minimum banding, is shown in FIG. 9B, overlaid with the solution from minimum-gradient searches. The trajectory established from the minimum gradient search is shown as line 220. The majority of the trajectory 220 follows these minimum sections (e.g. 225 and 230) of the map while abiding the restrictions for angular motion, as designed.

In another example embodiment, a quantitative evaluation of the degree of whitespace minimization may be determined. This may be done, for example, as follows. At each control point, the smallest value of whitespace within the full range of collimator angles (i.e. −90° to +90°) is identified. These minimum whitespace values are added together for all control points, in order to create the absolute minimum accumulated whitespace value that could possibly be achieved for this set of control points. The accumulated whitespace for each candidate trajectory (i.e. collimator motions that respect the dosimetric limitations described above) may then be compared to this minimum accumulated whitespace value.

For example, a ratio providing a measure of whitespace minimization may be obtained by dividing the accumulated whitespace for a given collimator trajectory by the minimum accumulated whitespace value. This quantity relates the physically achievable whitespace to the ideal whitespace.

A current focus in cranial radiotherapy is high-quality automation for the treatment of multiple brain metastases. An important parameter in these plans is the determination of a collimation angle which has the ability to not only collimate the BEV, such that each PTV can be tightly fitted, but that the anatomy between PTVs can be blocked during treatment in order to minimize dose to normal brain tissue between the PTVs. In arc therapy treatments of multiple metastases cases, which are delivered with a rotating gantry, the aforementioned whitespace methods can be applied in order to produce a suitable or optimized collimator angle for each control point. Combining all PTVs and applying the preceding whitespace reduction methods can produce a suitable collimator angle for preventing dose in the space(s) between PTVs.

Figure 10:
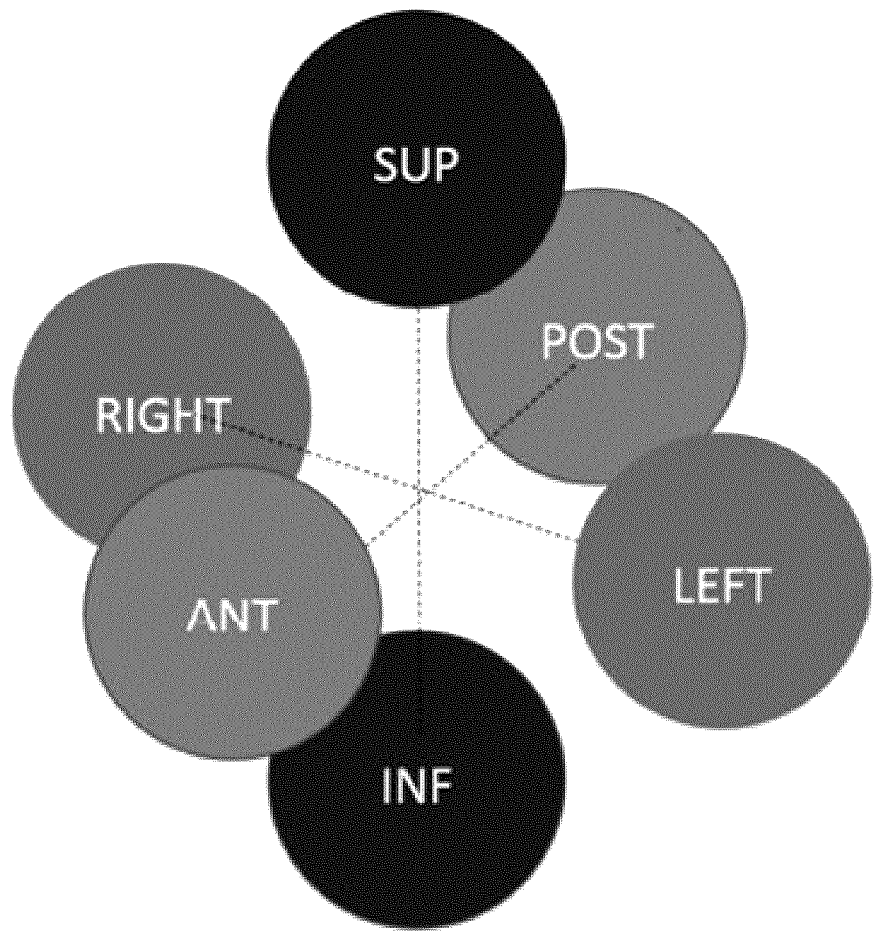
FIG. 10 shows three sets of stacked spheres in orthogonal directions.

This application of the previously described methods to address multiple PTVs can be understood with reference to an example illustrated in FIG. 10. This figure shows three cases of PTVs represented as orthogonally-positioned spheres (with a diameter of 2 cm), namely superior-inferior (sup-inf), left-right, and anterior-posterior (ant-post) spatial orientations. These spatial configurations were used to generate generate whitespace maps according to the methods described above.

Figure 11A:
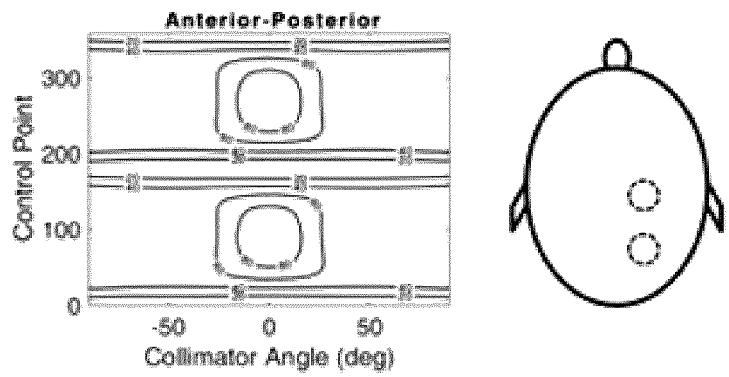
FIGS. 11A-11C show the three orthogonal scenarios of 2 cm spheres; A) Anterior-Posterior, B) Superior-Inferior C) Right-Left. The images on the left show normalized and low-pass filtered whitespace maps generated in each of these scenarios with the same methods described above, while the images on the right show the relevant planes to present anatomical context for placement of the spheres.
Figure 11B:
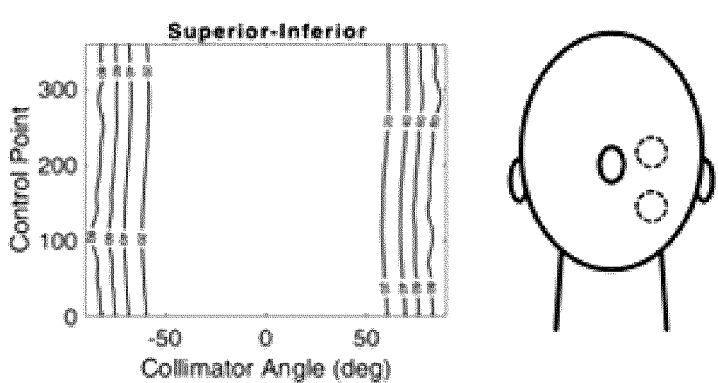
Figure 11C:
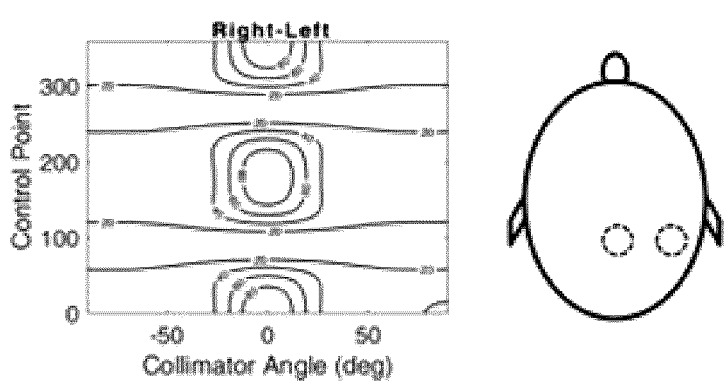

For each of the orthogonally positioned spheres, the same coplanar couch-gantry trajectory supplied the BEV. In one degree increments, the BEV was assessed for whitespace and the results were compiled into a two-dimensional whitespace map. The whitespace maps corresponding to each of these three cases are shown in FIGS. 11A-11C, alongside the sagittal, coronal, and axial planes to show anatomical context for the spheres. The isocentre for all three measurements was equidistant from both spheres.

Figure 12A:
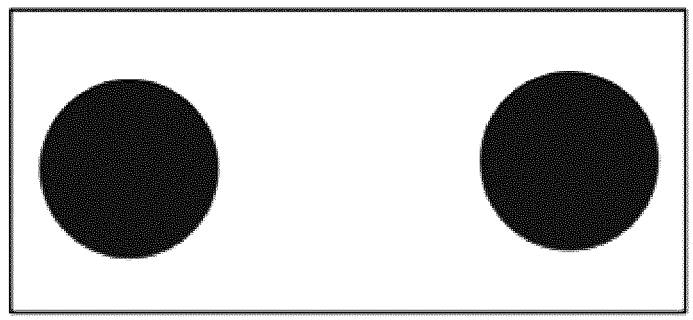
FIGS. 12A-12C depict geometries at which collimation angle selection is highly consequential in multiple metastasis; A) a beam's eye view (BEV) without MLC field shaping. Two circular target areas are indicated by dark circles, B) collimator angle providing horizontal leaf travel: worst-case optimization with maximum whitespace; C) collimator angle providing vertical leaf travel: optimal collimation leading to maximum shielding of normal tissues, minimizing whitespace.
Figure 12B:
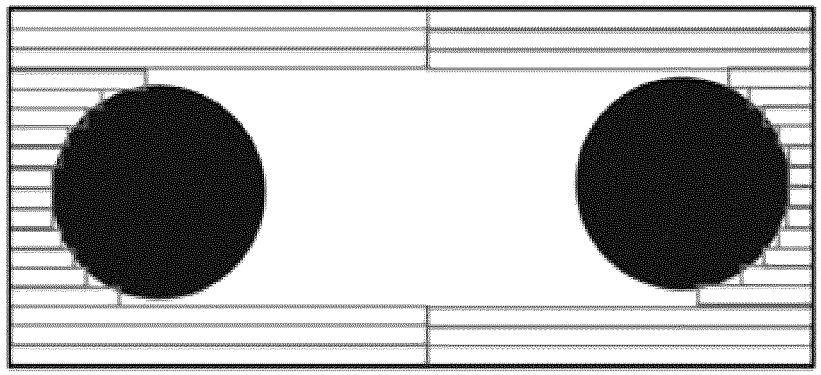

In each of these three scenarios, when collimating to both PTVs, there exist BEVs where the potential for non-optimal collimation angle is highly consequential on the normal tissue between volumes. The geometry of this scenario is displayed in FIG. 12A. In these cases, optimal collimator angle determination is important for limiting dose to normal tissues, and the consequence of an incorrect determination of angle is at its highest. In each of the three orthogonal sphere experiments, the consequential collimator angles present themselves as peaks (regions of approximately 100% normalized whitespace value) on the whitespace maps. These exist as island regions on the Anterior-Posterior plot (FIG. 11A) near control point 90 and control point 270, island regions on the Right-Left plot (FIG. 11C) near control points 0, 180 and 360, and as bands on the Superior-Inferior plot (FIG. 11B). These geometries would present the scenario depicted in FIG. 12B.

Figure 12C:
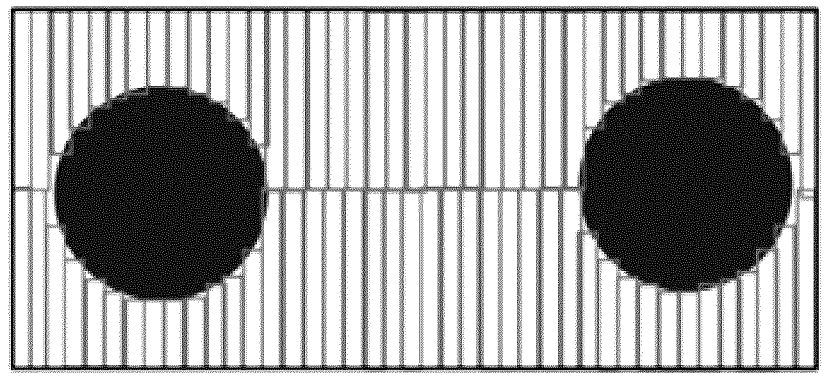

Successful collimation of the geometry as depicted in FIG. 12C leaves minimal whitespace in the aperture. While manual selection in this fixed aperture example seems intuitive, the solution to optimal collimator angle with multiple metastases is quickly confounded when solving every BEV in rotating treatment deliveries. Additionally, current convention is to establish a single collimator angle position for an entire treatment, leaving non-optimal collimator angles in many BEVs. These issues can be solved with the technologies described above and in the construction of whitespace maps as seen in FIGS. 11A-C. Using the whitespace maps to determine collimator angles with low whitespace can avoid geometries such as those seen in FIG. 12B and using dynamic collimator trajectories, suitable collimation, such as that shown in FIG. 12C, can be achieved throughout delivery.

It is noted that the methods disclosed herein are suitable for determining collimator trajectories for a wide variety of spatial profiles of PTVs and OARs (such as multiple overlapping or non-overlapping PTVs and/or OARs), and are not limited to cases in which the PTV has a well-defined axis associated therewith.

For example, the methods disclosed herein may be employed to determine suitable collimator angles and collimator trajectories for PTV and OAR spatial configurations that would not suitable for collimator angle determination using previous techniques. Unlike prior methods based exclusively on principal component analysis, the whitespace minimization methods disclosed herein introduce additional functionality and flexibility by allowing for different functional forms of weighting factors to determine how to address the presence of OARs that overlap with the PTV based on position of the OAR pixels (i.e. entrance dose versus exit dose).

In some example embodiments described herein, a bi-directional gradient searching method may be employed to identify candidate collimator trajectories. The aforementioned gradient-based trajectory identification method (illustrated, for example, in FIG. 8) has searched in a uniform direction for solutions based on minimizing gradient search of whitespace values. In expanded terms, this means searching the next control point for the allowed collimator angle which corresponds to the least amount of whitespace. The allowed collimator angles may be identified based on a clinically defined rule in units of degrees per control point. The identifications of suitable trajectories can be further diversified if the gradient search is applied in multiple directions. Clinically speaking, the deliverability of an arc in different rotational directions (clockwise/counterclockwise) are equivalent, and hold no bearing in the designation of the direction of treatment. However, collimator trajectory direction can result in some consequence, as continuous low-value whitespace may be more accessible while gradient searching from different directions.

Figure 13:
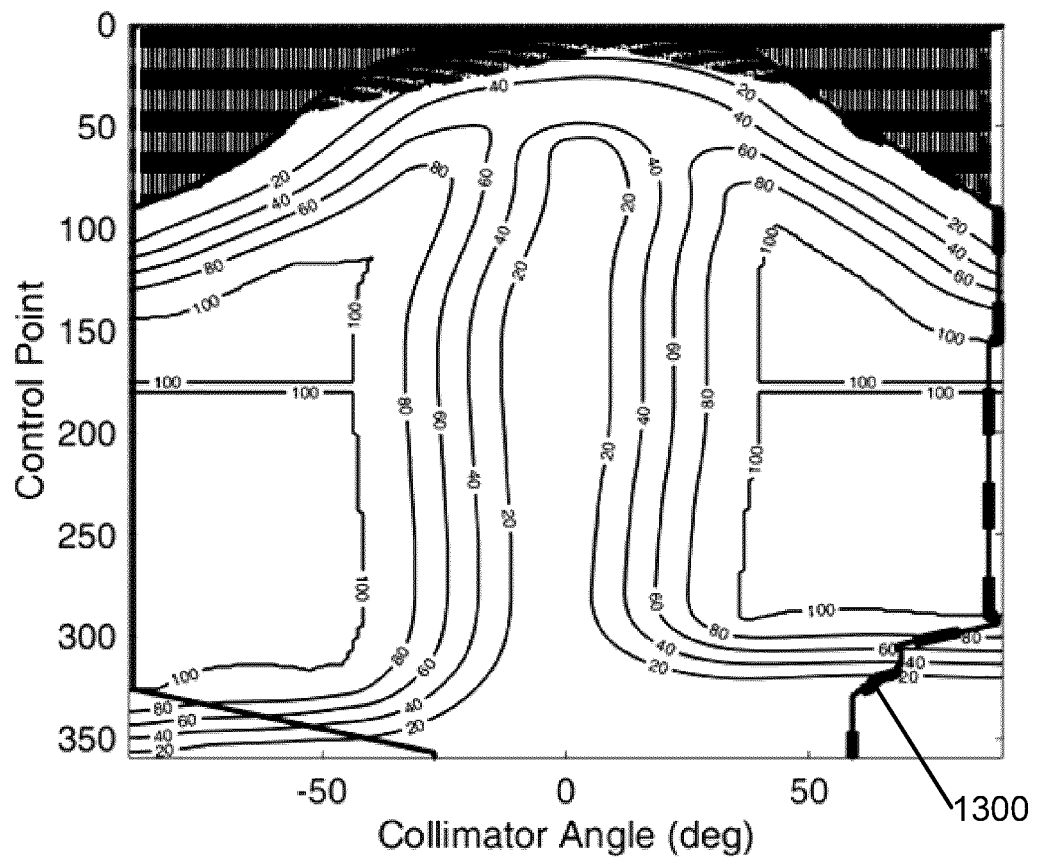
FIG. 13 shows a fictional whitespace map with a large U-shaped high-value region shielding a low-value region.
Figure 14:
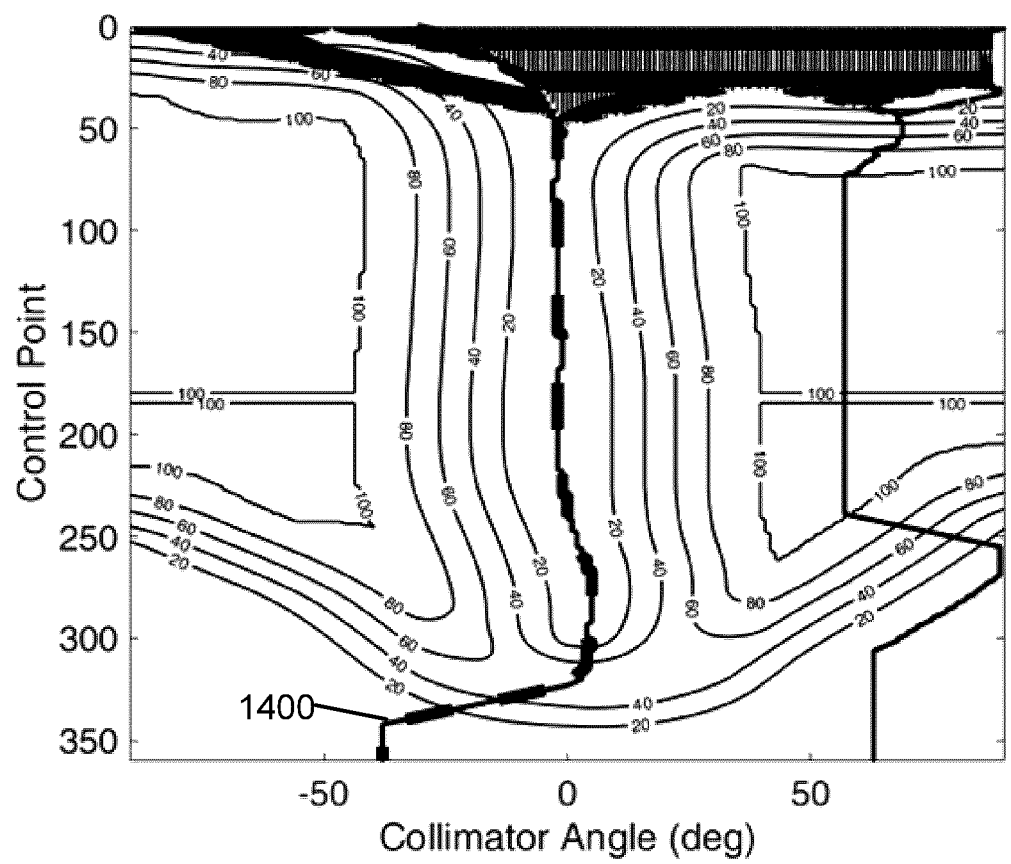
FIG. 14 shows fictional whitespace map with a large U-shaped high-value region shielding a low-value region.

As an illustrative example, FIGS. 13 and 14 show the presence of a U-shaped pattern of high whitespace, shielding a low whitespace region in a whitespace map. While attempting to identify a trajectory travelling from CP-1 to CP-end where CP-1 is control point 1 and CP-end is the control point at the end of the treatment, the gradient search will choose to always circumvent the high whitespace region, if possible. Conversely, if identifying trajectories travelling from CP-end to CP-1, the gradient search may lead to the internal void of the U-shape, which could possess regions of low-whitespace.

As the trajectory always searches for a path of least resistance, it will always aim to circumvent high-value regions. Lines 20, 40, 60, 80 and 100 indicate candidate trajectories starting from all possible starting points. Trajectory 1300 is the best choice, with the lowest accumulated whitespace.

With the trajectory travelling from CP-1 to CP-end (the initial calculation illustrated in FIG. 13), the best score of accumulated whitespace is 1944 normalized units of whitespace.

FIG. 14 illustrates the case where the map of FIG. 13 has been reversed, which is equivalent to searching in the opposite direction. Lines 20, 40, 60, 80 and 100 indicate candidate trajectories starting from all possible starting points, and the trajectory 1400 is the best choice, with the lowest accumulated whitespace. Reversing the direction of travel from CP-end to CP-1, results in a best score of accumulated whitespace of 1511 normalized units of whitespace, an improvement of 23%.

Additionally, using bi-directional gradient searching, all candidate trajectories from both directions can be pooled into a ranked database to identify which candidates illustrate features that would be optimal for treatment. Segments of these candidate trajectories that are particularly 'good' may be identified by long continuous stretches of control points which feature whitespace values less than some threshold (e.g. the threshold may be the mean of the map—this value is arbitrary). Such segments may be identified as desirable portions of a trajectory. By cataloguing many segments, a final trajectory may be developed by stitching these good segments into a new, previously unseen trajectory featuring highlights from all candidates. The accumulated whitespace for the new trajectory may be computed and compared to that for the trajectories in the database.

In order to directly compare the success of a given candidate trajectory, its accumulated whitespace can be quantified in terms of the best possible score. This score may be generated by identifying the angle corresponding to a minimum whitespace value for each control point on the map. As these angles could be largely separated and violate the rule established of maximum degrees per control point, it may not be feasible for delivery. However this would correspond to a lower bound in terms of the possible accumulated whitespace in a candidate trajectory. The quality of a trajectory could thus be quantitatively expressed as $$\text{Score} = \frac{\sum_{i=1}^{end} T_n(i)}{\sum_{i=1}^{end} T_{min}(i)} \times 100\%$$

where i is the control point index, $T_n(i)$ is the whitespace value of candidate trajectory n at control point i, and $T_{min}(i)$ is the minimum whitespace value at control point i. This calculation also removes the meaning of the raw accumulated scores, which often provide little context. Such a score may be displayed to a user.

Figure 15:
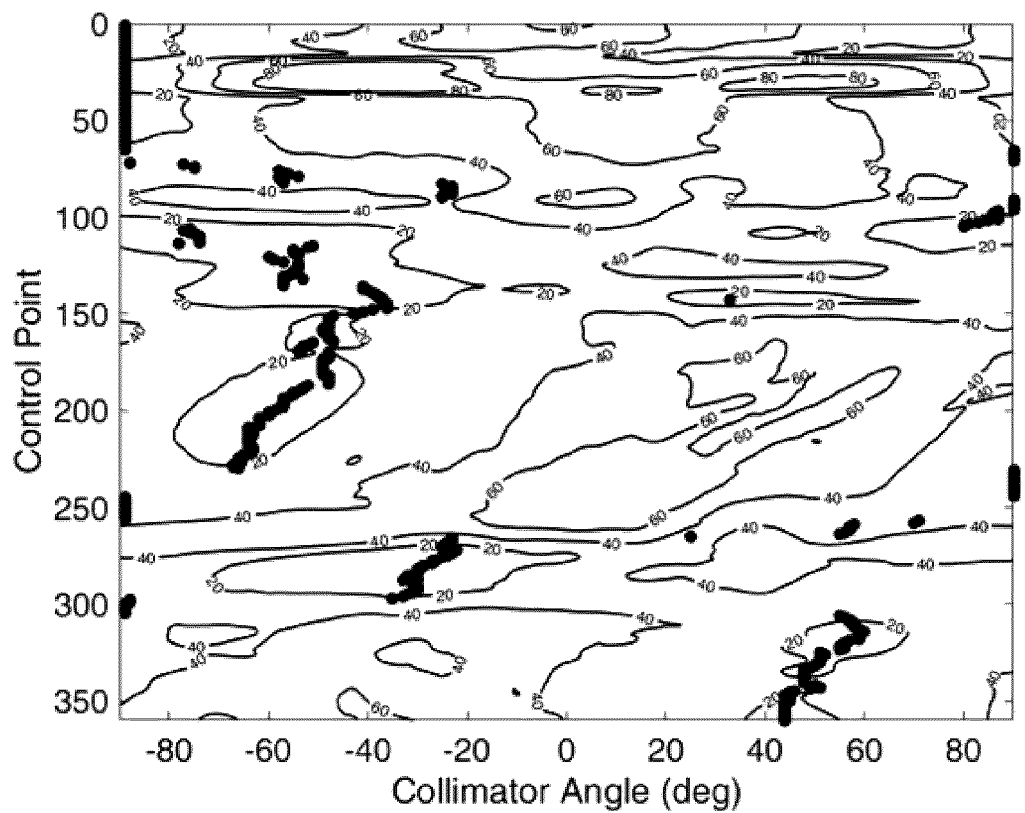
FIG. 15 illustrates the identification of the minimum whitespace value at each control point in the whitespace map. The cumulative score in this trajectory is 6036 normalized whitespace units.

An example calculation for a whitespace map is shown in FIG. 15, illustrating the identification of minimum coordinates for each control point in the whitespace map. The cumulative score in this trajectory is 6036 normalized whitespace units.

The trajectory denoted by the line 215 in FIG. 9A has the lowest accumulated whitespace of all candidate trajectories with a score of 8269 normalized whitespace units.

Using the equations established above, the score for the dashed line trajectory is scored as:

$$\text{Score} = \left(\frac{8269}{6036} \times 100\%\right) = 137\%$$

Figure 16:
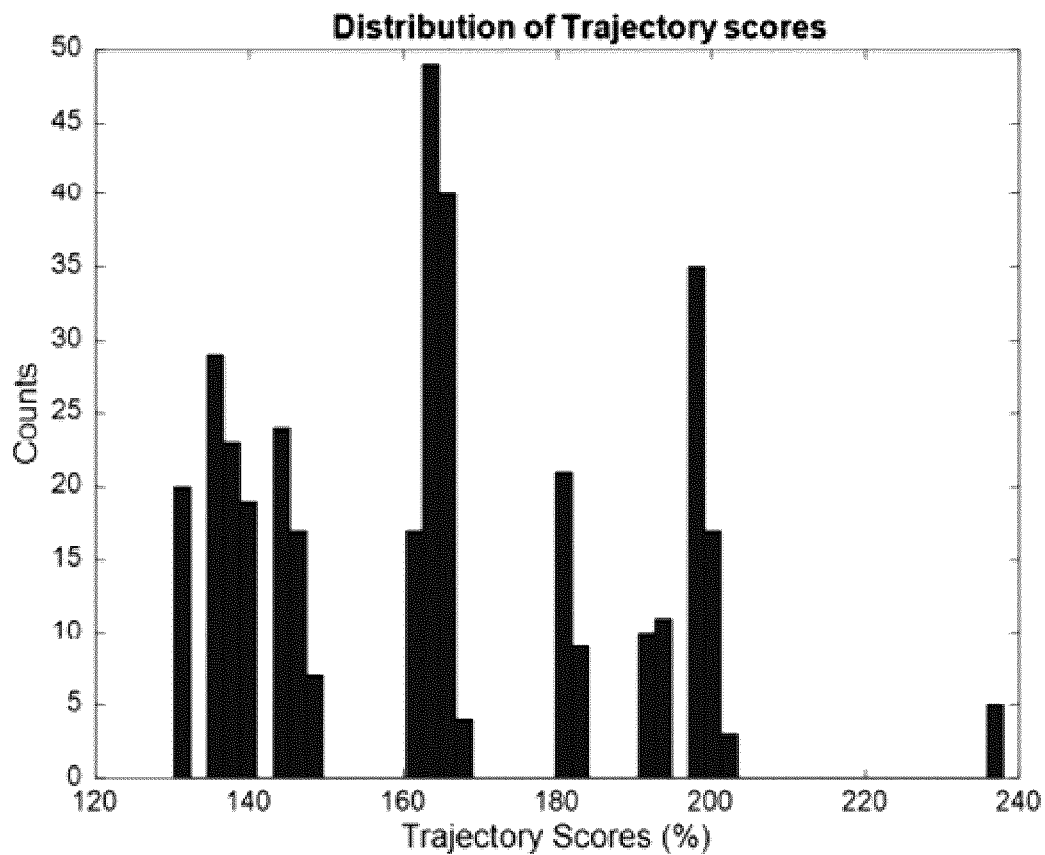
FIG. 16 shows the distribution of scores of candidate trajectories for each of the output solutions from FIG. 9A and those found searching from CP-end to CP-1 (N=360 trajectories).

Therefore this trajectory has a score of 137% of the best-case trajectory. All candidates could be similarly evaluated and the distribution of scores for solutions can be put into a histogram as shown in FIG. 16.

Figure 17:
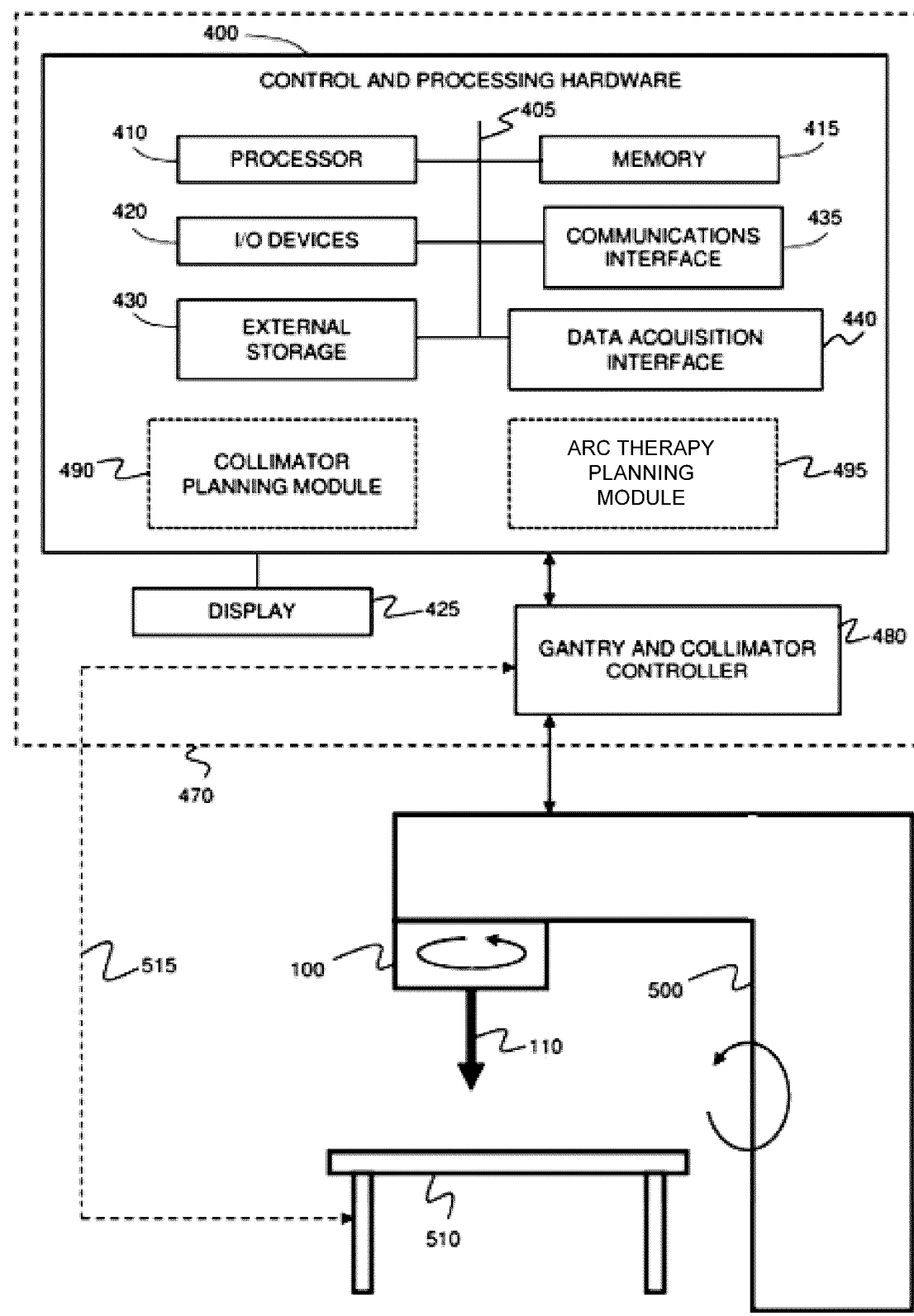
FIG. 17 shows an example radiation treatment system including a collimator planning module and a VMAT planning module.

FIG. 17 shows an example radiotherapy system of a type that may be used for performing arc therapy. The example system includes a gantry 500, which houses a radiation source (e.g. a linear accelerator), such that a radiation beam (e.g. an x-ray beam) is emitted and directed through a multileaf collimator 100. As described above, the multileaf collimator 100 includes a set of movable leaves for selectively altering a spatial profile of the radiation beam. Gantry 500 is rotatable for varying a beam angle of the radiation beam relative to the subject, and multileaf collimator 100 is rotatable relative to a beam axis of the radiation beam, for rotating the axis of the leaves relative to the subject. The subject is positioned on a treatment couch 510.

The rotation of gantry 500 and multileaf collimator 100 are controlled by a controller 480. Controller 480 may include motor controllers for controlling the operation of the motors that drive the rotation of gantry 500 and multileaf collimator 100. Controller 480 may also control the operation of the radiation source. As shown by the dashed line 515, controller 480 may also control the position and/or orientation of treatment couch 510. Controller 480 is operatively coupled to control and processing hardware 400. As shown in FIG. 17, controller 480 may optionally be directly integrated into a control and processing device 470, or may be provided as an external device.

As shown in the example embodiment illustrated in FIG. 17, the control and processing hardware 400 may include a processor 410, a memory 415, a system bus 405, one or more input/output devices 420, and a plurality of optional additional devices such as communications interface 435, display 425, external storage 430, and data acquisition interface 440. In one example implementation, the display 425 may be employed to provide a user interface for displaying aspects of the arc therapy plan and/or for providing input to control the operation of the system. As shown in FIG. 17, the display may be directly integrated into a control and processing device 470 (for example, as an embedded display), or may be provided as an external device (for example, an external monitor).

The aforementioned example methods for identifying a selected collimator trajectory and for controlling the rotation of the multileaf collimator 100 can be implemented via processor 410 and/or memory 415. As shown in FIG. 17, executable instructions represented as collimator planning module 490 are processed by control and processing hardware 400 to identify a suitable collimator trajectory that is associated with the control points to be employed by an arc therapy plan (for example a volumetric modulated arc therapy plan). The control and processing hardware 400 may include, for example, and execute instructions for performing one or more of the methods illustrated in FIGS. 7 and 8, or other methods described herein, or variants thereof. Such executable instructions may be stored, for example, in the memory 415 and/or other internal storage.

Control and processing hardware 400 may also include executable instructions for generating an arc therapy plan, as represented by arc therapy module 495, based on the previously defined control points (e.g. the gantry and/or couch trajectory) and the collimator trajectory. Alternatively, control and processing hardware 400 may be configured to transmit or otherwise provide the calculated collimator trajectory to an external arc therapy planning system, and to subsequently receive or otherwise obtain a arc therapy plan generated by the external planning system The foregoing description has described various methods in which accumulated whitespace is used as an objective function for assessing collimator trajectories. These methods may be generalized to cases in which other objective functions are used to assess alternative trajectories. For example, a metric based on whitespace may be combined (for example by averaging or taking a weighted sum or weighted product or the like) with one or more other metrics. A trajectory may be elected based on such an objective function. An example of another metric that could be included in an objective function is a measure of the collective magnitude of deviation of the angle of the collimator from an angle that is perpendicular to the longest axis of the target in the beam's eye view for each of the control points.

The methods described herein can be partially implemented via hardware logic in processor 410 and partially using the instructions stored in memory 415. Some embodiments may be implemented using processor 410 without additional instructions stored in memory 415. Some embodiments are implemented using the instructions stored in memory 415 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing hardware 400 may be provided as an external component that is interfaced to a processing device. Furthermore, although the bus 405 is depicted as a single connection between all of the components, it will be appreciated that the bus 405 may represent one or more circuits, devices or communication channels which link two or more of the components. For example, the bus 305 may include a motherboard. The control and processing hardware 400 may include many more or less components than those shown.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method for determining a collimator trajectory for controlling a multileaf collimator of a radiotherapy device during arc therapy, the method comprising:

calculating, for each control point of a set of control points to be employed for generating an arc therapy plan, a plurality of spatial measures corresponding to a set of different collimator angles of the multileaf collimator, wherein each spatial measure is based, at least in part, on a determination of a residual unblocked area residing between a planning target volume and leaves of the multileaf collimator, thereby generating two-dimensional spatial map data characterizing a dependence of spatial measures on control point and collimator angle;

processing the spatial map data to determine a selected collimator trajectory that reduces or minimizes a sum of spatial measures accumulated over the set of control points, the selected collimator trajectory associating a single collimator angle with each control point.

2. The method according to claim 1 wherein determining the selected collimator trajectory comprises constraining a change in collimator angle between two successive beam angles to not exceed a an achievable angular range that is achievable taking into account operating constraints of the multileaf collimator.

3. The method according to claim 1 wherein calculating the spatial measures comprises excluding from the planning target volume a portion of the planning target volume that spatially overlaps with an organ at risk.

4. The method according to claim 3 wherein the spatial measures are calculated for a plurality of organs at risk.

5. The method according to claim 1 wherein the spatial measures are calculated for a plurality of planning target volumes.

6. The method according to claim 1 wherein calculating the spatial measures comprises excluding from the planning target volume a portion of the planning target volume that is proximate to a portion of the planning target volume that spatially overlaps with an organ at risk.

7. The method according to claim 1 wherein calculating the spatial measures comprises excluding from the planning target volume a sub-portion of a portion of the planning target volume that spatially overlaps with an organ at risk.

8. The method according to claim 1 wherein calculating the spatial measures comprises excluding from the planning target volume a sub-portion of a portion of the planning target volume that spatially overlaps with two or more organs at risk.

9. The method according to claim 8 comprising calculating the sub-portion at least in part on a ranking of the two or more organs at risk.

10. The method according to claim 1 wherein a given spatial measure, at a given beam angle and a given collimator angle, is calculated according to the equation:

spatial measure=$A\_jaw-(A\_PTV-A\_PTVOAR)-A\_MLC$;

wherein A_jaw is an area defined by a minimum bounding box of the projected view of the planning target volume in the beam's eye view at the given collimator angle, A_PTV is an area of the planning target volume at the given beam angle, A_PTVOAR is an area of the planning target volume that spatially overlaps with the organ at risk, and A_MLC is an area within A_jaw that is collimated by the multileaf collimator.

11. The method according to claim 10 wherein A_PTV represents a plurality of planning target volumes that are spatially overlapping, such that A_PTV includes a sum of the areas of the plurality of planning target volumes minus areas of overlap among the plurality of planning target volumes.

12. The method according to claim 1 wherein a given spatial measure, at a given beam angle and a given collimator angle, is calculated according to the equation:

spatial measure=$w\_1*A\_jaw-(w\_2*A\_PTV-w\_3*A\_PTVOAR)-w\_4*A\_MLC$;

wherein A_jaw is an area defined by a minimum bounding box of the projected view of the planning target volume in the beam's eye view at the given collimator angle, A_PTV is an area of the planning target volume at the given beam angle, A_PTVOAR is an area of the planning target volume that spatially overlaps with the organ at risk, and A_MLC is an area within A_jaw that is collimated by the multileaf collimator; and w_1, w_2, w_3 and w_4 are weighting factors or functions.

13. The method according to claim 12 wherein the spatial measures are calculated such that w_4 compensates, at least in part, for interleaf leakage.

14. The method according to claim 12, wherein w_4 is calculated according to the equation:

$$w\_4=(1-\alpha)$$

where $\alpha$ is a parameter compensating for interleaf leakage.

15. The method according to claim 12, wherein w_4 is calculated according to the equation:

$$w_4=1\beta(1-e^{-\lambda\alpha})$$

where $\beta$ is a term that limits maximum impact of excessive MLC shielding on overall whitespace value; and $\lambda$ is a term that governs how quickly the weighting function will reach the maximum value assigned by $\beta$.

16. The method according to claim 12, wherein w_4 is calculated according to the equation:

$$w_4 = 1 - \beta\left(\frac{1}{1+\frac{1}{\lambda\alpha}}\right)$$

where $\alpha$ is a parameter compensating for interleaf leakage; $\beta$ is a term that limits maximum impact of excessive MLC shielding on overall whitespace value; and $\lambda$ is a term that governs how quickly the weighting function will reach the maximum value assigned by $\beta$.

17. The method according to claim 12 comprising calculating the spatial measures such that w_3 is selected so that the spatial measures exclude from the planning target volume a portion of the planning target volume that is proximal to an organ at risk.

18. The method according to claim 17 wherein the organ at risk comprises a plurality of organs at risk, and w_3 comprises a weighting function comprised of a contribution of each of the plurality of organs.

19. The method according to claim 1 comprising calculating a given spatial measure, at a given beam angle and a given collimator angle, according to the equation:

spatial measure=$w\_1*A\_jaw-w\_4*A\_MLC$;

wherein A_jaw is an area defined by a minimum bounding box of the projected view of the planning target volume in the beam's eye view at the given collimator angle, and A_MLC is an area within A_jaw that is collimated by said multileaf collimator; and wherein w_1 and w_4 are weighting factors or functions.

20. The method according to claim 1 comprising determining the collimator trajectory such that the selected collimator trajectory passes, at one of the control points having a maximum spatial measure associated therewith, through a collimator angle that exhibits a minimum spatial measure for the one of the control points having the maximum spatial measure associated therewith.

21. The method according to claim 1 wherein the selected collimator trajectory is determined by:
 a) selecting, at an initial control point, an initial collimator angle;
 b) randomly generating a test collimator trajectory, wherein the test collimator trajectory is generated by randomly altering the collimator angle between control points while constraining the change in collimator angle between successive control points;
 c) repeating step b) to generate a plurality of test collimator trajectories; and
 d) selecting the test collimator trajectory having a minimum accumulated spatial measure.

22. The method according to claim 21 wherein the initial collimator angle is selected by determining, at the initial control point, a collimator angle having a minimum spatial measure.

23. The method according to claim 21 wherein selecting the initial control point comprises identifying a control point having a maximum spatial measure associated therewith, and wherein the initial collimator angle is selected to be the collimator angle at the identified control point that exhibits a minimum spatial measure.

24. The method according to claim 1 wherein the selected collimator trajectory is determined by:
 a) determining, based on an initial collimator angle at an initial control point, a subsequent collimator angle for a subsequent control point, wherein the subsequent collimator angle is a collimator angle that yields a minimum spatial measure, wherein the subsequent collimator angle is constrained within a prescribed angular range;
 b) utilizing the subsequent collimator angle from step a) as the initial collimator angle for the subsequent control point, and repeating step a);
 c) repeating step b) for each control point to obtain a candidate collimator trajectory;
 d) repeating steps a)-c) for different initial collimator angles in order to obtain a set of candidate trajectories, wherein each candidate trajectory corresponds to a different initial control angle at the initial control point; and
 e) selecting the candidate collimator trajectory having a minimum accumulated spatial measure.

25. The method according to claim 1 wherein the subsequent control points are selected in a forward direction or a reverse direction among the set of control points.

26. The method according to claim 1 further comprising:
determining, at each control point, a minimum spatial measure from the spatial measures associated with the set of different collimator angles;
calculating a sum of the minimum spatial measures over the set of control points associated with the arc therapy plan, thereby calculating a minimum accumulated spatial measure; and
comparing the minimum accumulated spatial measure to the sum of the accumulated spatial measures over the selected collimator trajectory to obtain a quantitative measure of a degree of optimization associated with the selected collimator trajectory.

27. The method according to claim 1 wherein successive control points differ according to a change in beam angle.

28. The method according to claim 1 wherein successive control points differ according to a change of one or more of beam angle and an angle of a treatment couch.

29. The method according to claim 1 wherein the collimator trajectory is selected to pass, at a control point having a maximum spatial measure associated therewith, through a collimator angle that exhibits a minimum spatial measure.

30. The method according to claim 1 wherein the arc therapy plan is a volumetric modulated arc therapy plan.

31. The method according to claim 1 comprising calculating a longest axis of a projection of the planning target volume for one or more of the control points.

32. The method according to claim 31 comprising calculating a collimator angle matching parameter indicative of a degree to which the collimator angles of the arc therapy plan deviate from corresponding collimator angles for which a direction of motion of leaves of the collimator is orthogonal to the longest axis of the projection of the planning target volume.

33. The method according to claim 32 comprising calculating the spatial measures at least in part, on an accumulated value of the collimator matching parameter.

34. The method according to claim 1 comprising applying an oscillation to the collimator angle.

35. The method according to claim 1 wherein a given spatial measure is calculated according to the equation:

$$\text{spatial measure} = w\_WS * M\_ws + w\_PCA * M\_PCA;$$

wherein $M\_ws$ is a whitespace metric, $w\_WS$ is a first weighting factor, $M\_PCA$ is a collimator suitability metric, and $w\_PCA$ is a second weighting factor.

36. The method according to claim 1 comprising normalizing the spatial map data.

37. The method according to claim 1 comprising low-pass spatial filtering the spatial map data.

38. The method according to claim 1 wherein each of the control points corresponds to a different beam angle.

39. A method according to claim 1 comprising controlling the radiotherapy device, the radiotherapy device comprising a radiation source, a rotatable gantry, and the multileaf collimator supported by the rotatable gantry, wherein the multileaf collimator is rotatable relative to a beam axis of a radiation beam produced by the radiation source, the method comprising:
generating, based on the selected collimator trajectory and the set of control points, an arc therapy plan;
controlling the gantry such that the gantry is rotated according to the arc therapy plan; and
controlling the multileaf collimator such that said multileaf collimator is rotated and positioned according to the arc therapy plan.

* * * * *

UNITED STATES PATENT AND TRADEMARK OFFICE
CERTIFICATE OF CORRECTION

PATENT NO. : 10,525,283 B2
APPLICATION NO. : 16/083454
DATED : January 7, 2020
INVENTOR(S) : Robert Lee MacDonald, Alasdair Syme and Christopher G. Thomas It is certified that error appears in the above-identified patent and that said Letters Patent is hereby corrected as shown below:

In the Specification

In Column 18, Line 15, "For example, the methods disclosed herein may be employed to determine suitable collimator angles and collimator trajectories for PTV and OAR spatial configurations that would not suitable for collimator angle determination using previous techniques." is corrected to --For example, the methods disclosed herein may be employed to determine suitable collimator angles and collimator trajectories for PTV and OAR spatial configurations that would not be suitable for collimator angle determination using previous techniques.--

In the Claims

Column 24, Lines 44-64:
"24. The method according to claim 1 wherein the selected collimator trajectory is determined by: a) determining, based on an initial collimator angle at an initial control point, a subsequent collimator angle for a subsequent control point, wherein the subsequent collimator angle is a collimator angle that yields a minimum spatial measure, wherein the subsequent collimator angle is constrained within a prescribed angular range; b) utilizing the subsequent collimator angle from step a) as the initial collimator angle for the subsequent control point, and repeating step a); c) repeating step b) for each control point to obtain a candidate collimator trajectory; d) repeating steps a)-c) for different initial collimator angles in order to obtain a set of candidate trajectories, wherein each candidate trajectory corresponds to a different initial control angle at the initial control point; and e) selecting the candidate collimator trajectory having a minimum accumulated spatial measure."

Should read:
--24. The method according to claim 1 wherein the selected collimator trajectory is determined by: a) determining, based on an initial collimator angle at an initial control point, a subsequent collimator angle for a subsequent control point, wherein the subsequent collimator angle is a collimator angle that yields a minimum spatial measure, wherein the subsequent collimator angle is constrained within a prescribed angular range; b) utilizing the subsequent collimator angle from step a) as the initial collimator angle for the subsequent control point, and repeating step a); c) repeating step b) for each Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office* control point to obtain a candidate collimator trajectory; d) repeating steps a)-c) for different initial collimator angles in order to obtain a set of candidate trajectories, wherein each candidate trajectory corresponds to a different initial control collimator angle at the initial control point; and e) selecting the candidate collimator trajectory having a minimum accumulated spatial measure.--